ature Patent [19]

United States Patent [19]
Lifson et al.

[11] Patent Number: 4,795,739
[45] Date of Patent: Jan. 3, 1989

[54] METHOD OF INHIBITING HIV

[75] Inventors: Jeffrey D. Lifson, Menlo Park; Michael S. McGrath, Burlingame, both of Calif.; Hin-Wing Yeung, Kowloon, Hong Kong; Kou M. Hwang, Danville, Calif.

[73] Assignees: Gene Labs, Inc., Redwood City; Regents of University of California, Berkeley, both of Calif.

[21] Appl. No.: 56,558

[22] Filed: May 29, 1987

[51] Int. Cl.$^4$ .................. A61K 37/02; A61K 35/78; A61K 35/80; C07G 7/00
[52] U.S. Cl. .......................... 514/8; 514/12; 514/885; 530/370; 424/195.1
[58] Field of Search ............... 514/8, 12, 885; 530/370; 424/195.1

[56] References Cited

PUBLICATIONS

Kubota et al., "Conformation of Abortifacient Proteins; Tricosanthin, α-Momorcharin and β-Momorcharin" *Biochimica et Biophysica Acta* 871 (1986), 101–106.
Falasca et al., "Properties of the Ribosome-Inactivating Proteins Gelonin, *Momordica Charantia* Inhibitor, and Dianthins" *Biochemistry J.* (1982), 207, 505–509.
Barbieri et al., "Inhibition of Protein Synthesis in Vitro by a lectin from *Momordica Charantia* and by other Haemagglutinins" *Biochem J.* (1979) 182, 633–635.
Barbieri et al., "Inhibition of Protein Synthesis in Vitro by Proteins from the Seeds of *Momordica Charantia* (Bitter Pear Mellon)" *Biochem. J.* (1980) 186, 443–452.
Jilka et al., "In Vivo Antitumor Activity of the Bitter Melon (*Memordica Charantia*)" *Cancer Research* 43, 5151–5156, Nov. 1983.
Leung et al., "The Immunomodulatory and Antitumor Activities of Trichosanthin an Abortifacient Protein Isolated from *Tian-Hau-Fen Trichosanthes-Kirilowii*," *Asian Pac. J. Allergy Immunol.* 4(2) 1986, 111–120.
Leung et al., "The Immunosuppressive Activities of Two Abortifacient Proteins Isolated from the Seeds of Bitter Melon *Momordica-Charantia*," *Immunopharm.* 13(3), 1987, 159–172.

Armstrong, W. H., Presented at the International Conference of Aids, 23–25 Jun. 1986, Paris.
Barbieri, L. et al., Biochem J. 203:55 (1982).
Barnes, D. M., Science, 235:964 (1987).
Broder et al., Lancet ii:627 (1985).
Broder et al., Nature 325–:773 (1987).
Chan, W. Y. et al., Contraception, 29:91 (1984).
Chayt, K. J. et al., JAMA, 256:2356 (1986).
Coffin, J. et al., Science, 232:697 (1986).
Crowe, S., Mills, J. and McGrath, M. S., submitted for publication.
Curran, J. W. et al., Science, 229:1352 (1985).
Dalgliesh, A. G. et al., Nature, 312:763 (1984).
Fahey, J. L., Am J Me7, 76:95 (1984).
Foa-Tomasi, L. et al., Arch Virol, 71:323 (1982).
Foung, S. K. H. et al., Human Hybridomas and Monoclonal Antibodies, E. G. Engleman et al., Eds., Plenum Press, N.Y., p. 437 (1985).
Gartner S., Science, 233:215 (1986a).
Gartner S. et al., JAMA, 256, 2365 (1986b).
Gaspani-Compani, A., Biochem J., 186:439 (1980).
Gu, Zi-Wei et al., Acta Chemica Sinica, 43:943 (1984).
Ho, D. D. et al., J. Clin. Invest., 77:1712 (1986).

(List continued on next page.)

Primary Examiner—John Kight
Assistant Examiner—Nathan M. Nutter
Attorney, Agent, or Firm—Peter J. Dehlinger

[57] ABSTRACT

A method of inhibiting expression of HIV antigens in human blood cells infected with HIV. The infected cells are exposed to a plant protein or glycoprotein, such as trichosanthin or momorcharin, at a concentration sufficient to (a) produce a substantial reduction in the level of HIV antigen, and (b) effect a selective reduction in the number of HIV-infected cells, with respect to uninfected cells of the same type. The method is used to treat HIV infection in humans. In another aspect, the invention includes a method of screening drug agents effective in treating HIV infection in humans.

13 Claims, 8 Drawing Sheets

OTHER PUBLICATIONS

Hsu, K. J. et al., Acta Zool Sin, 22:149 (1976).
Hoffman, A. E. et al., Virology, 147:326 (1985).
Hwang, Y. N., Chinese J Integrated Trad and Western Medicine, 7:154 (1987).
Irvin, J. D., Pharmacol Ther, 21:371 (1983).
Kao, H. et al., Acta Biol Exp Sin, 11:253 (1978).
Kennedy, R. C. et al., Science, 231:1556 (1986).
Kezhan, Pan et al., Supplement of Proc of China-Japan Bilateral Symposium on Biophys, Wuxi, China (May 1985).
Klatzmann, D. et al., Science, 225:59 (1984a).
Klatzmann, D. et al., Nature, 312:767 (1984b).
Koenig, S. et al., Science, 233:1089 (1986).
Kuo-Fen, C. et al., Obs and Gyn, 59(4):494 (1982).
Law, L. K. et al., J Reprod Fert, 69:597 (1983).
Licastro, F. et al., Virchows Arch B Cell Path, 33:257 (1980).
Lifson, J. D. et al., Science, 232:1123 (1986a).
Lifson, J. D. et al., Nature, 323:725 (1986b).
Lifson, J. D. et al., J. Exp. Med., 164:2101 (1986c).
Lifson, J. D., J. Exp. Med., 164:2101 (1986c).
Lin, J. Y. et al., Cancer Res., 30:2431 (1970).
Lin, J. Y. et al., Toxicon, 16:653 (1978).
Maddon, J. P., Cell, 47:333 (1986).
McCormick, J. B. et al., Lancet, ii:1367 (1984).
McDougal, J. S., Science, 231:382 (1985a).
McDougal, J. S., J. Immunol., 135:3151 (1985b).
McDougal, J. S., J. Immunol., 137:2937 (1986).
Olnes, S. et al., in Molecular Action of Toxins and Viruses, 51–105 Elsevier, Amsterdam (1982).
Popovic, M. et al., Science, 224:497 (1984).
Roberts, W. K., Biochemistry, 18:2615 (1979).
Salvedt, E., Biochim., Biophys. Acta., 451:536 (1976).
Sodroski, J. et al., Nature, 322:470 (1986).
Spreafico, F. et al., Int. J. Immunopharmac, 5(4): 335 (1983).
Stanley, W. S. et al., Proc. Nat. Acad. Sci., U.S.A. 76:303 (1979).
Steicher, H. Z. et al., JAMA, 256:2390 (1986).
Stirpe, F. et al., J. Biol. Chem., 255:6947 (1980).
Stirpe, F. et al., Biochem. J. 195:399 (1981).
Takemoto, D. J. et al., Prep. Biochem., 12(4):355 (1982).
Takemoto, D. J. et al., Prep. Biochem., 13(4):371 (1983a).
Takemoto, D. J. et al., Prep. Biochem., 13(5):397 (1983b).
Wang, Yu et al., Int. Symposium on Org. Chem. of Medicinal Natural Products, Shanghai, China (Nov. 1985).
Xiong, Y. Z. et al., Acta. Zool. Sin., 11:236 (1976).
Xuejan, Z. et al., Nature, 321:477 (1986).
Yarochoan, R. et al., Lancet, i:575 (1986).
Yarochoan, R. et al., Lancet, i:132 (1987).
Yeung, H. W. et al., in Adv. in Chinese Medicinal Materials Res., edited by H. M. Change et al., World Scientific Pub., Singapore, p. 311 (1985).
Yeung, H. W. et al., Int. J. Peptide Protein Res., 27:325 (1986).
Fernandez-Puentes et al., Cell, vol. 20, 769–775, Jul. (1980). Viral Infection Permeabilizes Mammalian Cells to Protein Toxins.
Fernandez-Puentes, Molecular and Cellular Biochemistry 50, 185–191 (1983). Permeability to Alpha Sarcin in Virus-Infected Cells.

METHOD OF INHIBITING HIV

FIELD OF THE INVENTION

The present invention relates to a method of inhibiting the expression of HIV proteins in human T cells and monocyte/macrophages, as a method of treating HIV infection in humans.

REFERENCES

Armstrong, W. H., Presented at the International Conference on AIDS, 23–25 June, 1986, Paris.
Barbieri, L. et a,, Biochem J, 182:633 (1979).
Barbieri, L. et al, Biochem J, 186:443 (1980).
Barbieri, L. et al, Biochem J, 203:55 (1982).
Barnes, D. M., Science, 235:964 (1987).
Broder et al, Lancet, ii:627 (1985).
Broder et al, Nature 325:773 (1987).
Chan, W. Y. et al, Contraception, 29:91 (1984).
Chayt, K. J. et al, JAMA, 256:2356 (1986).
Coffin, J. et al, Science, 232:697 (1986).
Crowe, S., Mills, J., and McGrath, M. S., submitted for publication.
Curran, J. W. et al, Science, 229:1352 (1985).
Dalgliesh, A. G. et al, Nature, 312:763 (1984)
Fahey, J. L., Am J Med, 76:95 (1984).
Falasca, A. et al, Biochem J, 207:505 (1982).
Foa-Tomasi, L. et al, Arch Virol, 71:323 (1982).
Foung, S. K. H. et al, Human Hybridomas and Monoclonal Antibodies, E. G. Engleman et al, eds, Plenum Press, New York, p.437 (1985).
Gartner S., Science, 233:215 (1986a).
Gartner S. et al, JAMA, 256, 2365 (1986b).
Gaspani-Campani, A., Biochem J, 186:439 (1980).
Gu, Zi-wei, et al, Acta Chemica Sinica, 43:943 (1984).
Ho, D. D. et al, J Clin Invest, 77:1712 (1986).
Hsu, K. J., et al, Acta Zool Sin, 22:149 (1976).
Hoffman, A. D. et al, Virology, 147:326 (1985).
Hwang, Y. N., Chinese J Integrated Trad and Western Medicine, 7:154 (1987).
Irvin, J. D., Pharmacol Ther, 21:371 (1983).
Jilka, C. et al, Cancer Res, 43:5151 (1983).
Kao, H., et al, Acta Biol Exp Sin, 11:253 (1978).
Kennedy, R. C., et al, Science, 231:1556 (1986).
Kezhan, Pan, et al, Supplement of Proc of China-Japan Bilateral Symposium on Biophys, Wuxi, China (May, 1985).
Klatzmann, D., et al, Science, 225:59 (1984a).
Klatzmann, D., et al, Nature, 312:767 (1984b).
Koenig, S., et al, Science, 233:1089 (1986).
Kubota, S. et al, Biochim Biophys Acta, 871:101 (1986).
Kuo-Fen, C. et al, Obs and Gyn, 59(4):494 (1982).
Law, L. K. et al, J Reprod Fert, 69: 597 (1983).
Licastro, F. et al, Virchows Arch B Cell Path, 33:257 (1980).
Lifson, J. D. et al, Science, 232:1123 (1986a).
Lifson, J. D. et al, Nature, 323:725 (1986b).
Lifson, J. D., J Exp Med, 164:2101 (1986c).
Lin, J. Y., et al, Cancer Res, 30:2431 (1970).
Lin, J. Y., et al, Toxicon, 16:653 (1978).
Maddon, J. P., Cell, 47:333 (1986).
McCormick, J. B. et al, Lancet, ii:1367 (1984).
McDougal, J. S., Science, 231:382 (1985a).
McDougal, J. S., et al, J Immunol, 135:3151 (1985b).
McDougal, J. S., et al, J Immunol, 137:2937 (1986).
Olnes, S. et al in Molecular Action of Toxins and Viruses, 51-105 Elsevier, Amsterdam (1982).
Popovic, M. et al, Science, 224:497 (1984).
Roberts, W. K., Biochemistry, 18:2615 (1979).
Salvedt, E., Biochim, Biophys Acta, 451:536 (1976).
Sodroski, J., et al, Nature, 322:470 (1986).
Spreafico, F. et al, Int. J. Immunopharmac, 5(4):335 (1983).
Stanley, W. S. et al, Proc Nat Acad Sci, USA, 76:303 (1979).
Steicher, H. Z. et al, JAMA, 256:2390 (1986).
Stirpe, F., et al, J Biol Chem, 255:6947 (1980).
Stirpe, F., et al, Biochem J, 195:399 (1981).
Takemoto, D. J. et al, Prep Biochem, 12(4):355 (1982).
Takemoto, D. J. et al, Prep Biochem, 13(4):371 (1983a).
Takemoto, D. J. et al, Prep Biochem, 13(5) 397 (198bb).
Wang, Yu, et al, Int Symposium on Org Chem of Medicinal Natural Products, Shanghai, China (November, 1985).
Xiong, Y. Z., et al, Acta Zool Sin, 11:236 (1976).
Xuejan, Z. et al, Nature, 321:477 (1986).
Yarochan, R. et al, Lancet, i:575 (1986).
Yarochan, R. et al, Lancet, i:132 (1987).
Yeung, H. W., et al, in Adv in Chinese Medicinal Materials Res, edited by H. M. Change et al, World Scientific Pub, Singapore p. 311 (1985).
Yeung, H. W. et al, Int J. Peptide Protein Res, 27:325 (1986).

BACKGROUND

Human Immunodeficiency Virus (HIV) is a retrovirus which is the etiological agent for acquired immune deficiency syndrome (AIDS) and a spectrum of related disorders (Coffin). The virus is transmitted by parenteral inoculation and/or intimate sexual contact. It is estimated that approximately 2 million people in the United States are infected with HIV at present, and current projections are that a majority of those now infected will develop AIDS or a significant clinical AIDS-related disease within a 7–10 year follow-up period (Barnes).

HIV is tropic and cytopathic for peripheral blood cells which express the cell surface differentiation antigen CD4 (T4, leu3). The viral tropism is believed to result from interactions between CD4 and the envelope glycoprotein of HIV. These interactions appear to be involved in the process by which HIV infects susceptible cells, and also underlie the mechanism by which HIV induces cell fusion in T cells (Lifson, 1986a, 1986b; Dalgleish; Klatzman, 1984a, 1984b; Maddon; McDougal, 1985a, 1085b; Sodroski). The cell fusion process, which leads to cell death, may, in turn, contribute to the progressive depletion of CD4 cells which charaterizes AIDS, and which is likely to be a major factor contributing to HIV-induced immunocompromise and its secondary consequences, opportunistic infections and neoplasms (Fahey).

The host cell range for the HIV virus includes, in addition to CD4+T cells, cells of the mononuclear phagocytic lineage, including peripheral blood monocyte/macrophages (Crowe; Gartner, 1986a, 1986b; Koenig; Ho; Chayt; Armstrong; Steicher), Langerhans cells of the skin, and dendritic reticulum cells within the lymph nodes. Mononuclear phagocytes may be a primary target cell for HIV infection within the central nervous system (Koenig; Gartner, 1986b). Cells of the macrophage lineage are likely to represent a major viral reservoir in vivo, and through their interactions with T cells, may contribute to the development and pathogenesis of AIDS and related clinical diseases (Crowe). Experiments conducted in support of the present invention suggest that a large percentage of monocyte/macrophages derived from HIV-infected individuals are capable of expressing HIV antigens, indicating widespread infection of the macrophage precursors. There is also evidence that macrophages expressing the HIV surface antigen may interact and fuse with CD4+T cells, leading to destruction of the crucial T cells (Crowe).

Intensive efforts to develop therapies which can prevent or block the development of serious clinical symptoms in HIV-infected individuals are under way. For the most part, these efforts have focused on the use of nucleotide analogue drugs which inhibit reverse transcriptase activity in virus-infected cells (Yarochan, 1986, 1987; Broder). These drugs would be expected to selectively inhibit new viral infection of cells, such as T cells and monocyte/macrophages, since reverse transcriptase is required for early viral infection. However, once viral infection is established in a cell, and viral replication is then carried out using host cell enzymes, the reverse transcriptase inhibitors would be expected to have limited inhibitory effect on viral replication and expression of viral antigens on the host cell surface. Although indications of some beneficial clinical effects have been observed, the early clinical testing results have provided little evidence that these drugs will be effective against later-stage progression of HIV infection to serious clinical diseases.

SUMMARY OF THE INVENTION

It is one general object of the invention to provide a method of inhibiting HIV antigen expression in HIV-infected human T cells and monocyte/macrophages, as a method of treating HIV infection in humans.

Another object of the invention is to provide a method of inhibiting HIV replication in infected T cells and monocyte/macrophages.

A related object of the invention is to provide an improved drug therapy for treating HIV infection in humans.

Still another object of the invention is to provide a method for screening drug agents for effectiveness against the expression of HIV antigens in infected blood cells.

The invention includes, in one aspect, a method of treating HIV-infected cells. The method includes exposing the infected cells to trichosanthin (TCS) or alpha or beta momorcharin (MMC), identified herein as anti-HIV proteins, at a concentration which is effective to (a) produce a substantial reduction in viral antigen expression in the cells, and (b) effect a selective reduction in the number of viable infected cells relative to non-infected cells of the same type. When infected cells are exposed to the anti-HIV proteins in culture, the cells show a rapid and nearly complete loss of viral antigen expression, as evidenced either by the loss of HIV envelope protein on the surface of infected T lymphocytes, or loss of HIV core protein in infected monocyte/macrophages. Tppically, the concentration of anti-HIV protein to which the cells are exposed is between about 0.3 and 3 $\mu$g/ml.

The ability of the anti-HIV proteins to inhibit HIV antigen expression in infected cells is exploited, according to another aspect of the invention, for treating HIV infection in humans. In the treatment method, HIV seropositive individuals, or individuals who have otherwise been exposed to the virus, are treated with the anti-HIV protein. The amount of protein which is administered is that amount effective to produce a substantial reduction in the level of viral antigen expression in the patient's HIV-infectable blood cells, such as T lymphocytes and/or monocyte/macrophages. Preferably the amount of drug administered is also effective to selectively reduce the number of viable infected cells relative to uninfected cells from the same cell type.

The invention als includes a method of screening therapeutic drug agents in vitro for effectiveeess against HIV-related diseases, such as AIDS, in humans. In this method, cultured, HIV-infected cells are first assayed for level of HIV expression, for example, the expression of HIV-specific proteins on the cell surface of infected T lymphocytes, or expression of viral core protein in monocyte/macrophages as measured by indirect immunofluorescence analysis. In the case of cultured monocyte/macrophages which are isolated from infected individuals, the cells are preferably cultured for several days before drug treatment, to allow for the development of maximum viral antigen expression in the infected cells. The cultured cells are exposed to the agent being screened, at selected concentrations, and the inhibition of viral antigen expression is followed at suitable intervals thereafter.

Drug screening by this method has been used to show that the anti-HIV proteins identifed herein effectively reduce viral antigen expression, as measured by either viral antigen displayed on the surface of infected cells, or viral antigen present predominantly in intracellular form, to background or near-background levels within a period of about 5–12 days after a single exposure to the protein. By contrast, several reverse transcriptase inhibitors, including ribavarin, phosphonoformate, phosphonoacetate, and azidothymidine, produce only partial inhibition of viral protein expression. The method is proposed for testing a variety of cytotoxic proteins, such as gelonin, wheat germ inhibitor, pokeweed antiviral protein, and other plant cytotoxins, bacterial cytotoxins, and cytotoxic peptide fragments of identified anti-HIV proteins, including peptide fragments of TCS and MMC.

These and other objects and features of the invention will become more fully apparent when the following detailed description of the invention is read in conjunction with the accompanying drawings, wherein:

antibody (frames at the left) or anti-HIV anti-body (frames at the right) followed by fluroescein-labeled anti-human antibody for uninfected T cells (4A,B); HIV-infected T cells (4C,D); and uninfected or HIV-infected T cells 16 days after exposure to 10 μg/ml TCS (4E,F) or MMC (4G,H).

Figure 5:
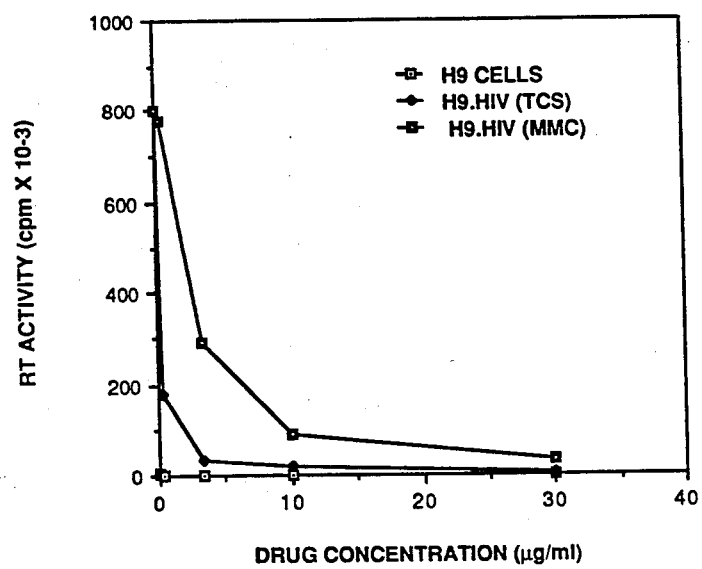
Figure 11:
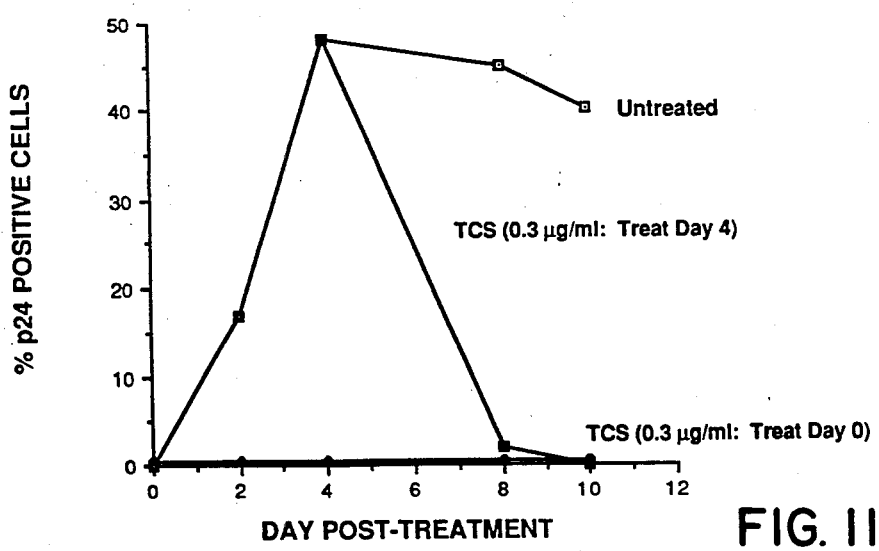
Figure 6:
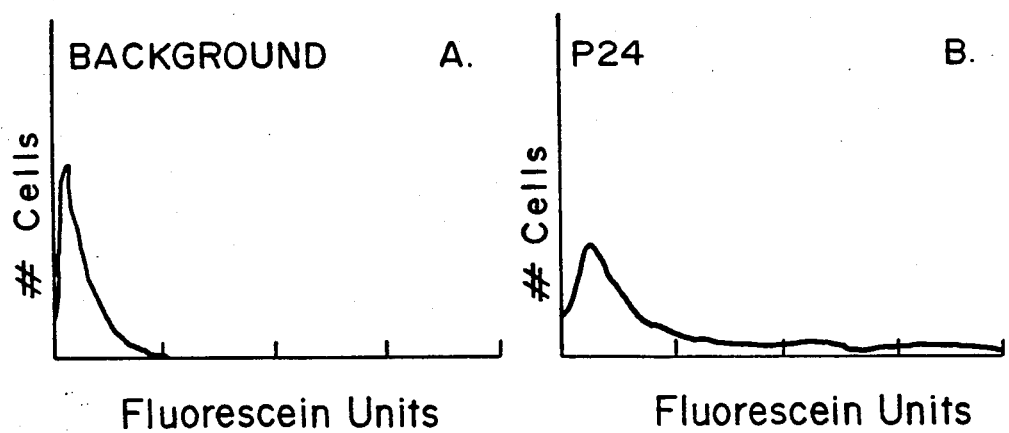
Figure 7:
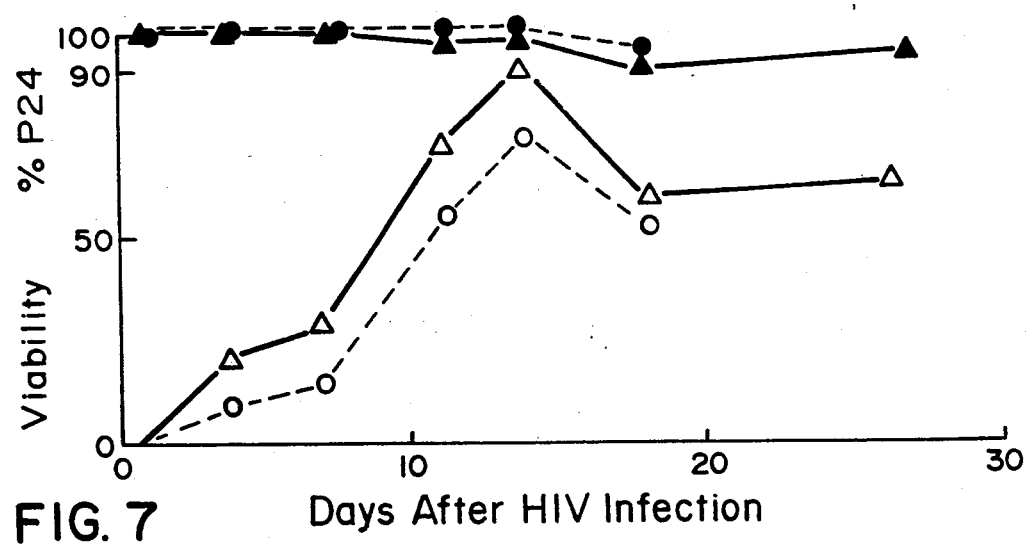
Figure 9:
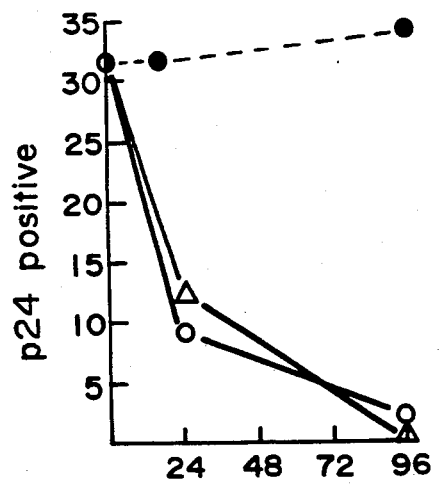
Figure 10:
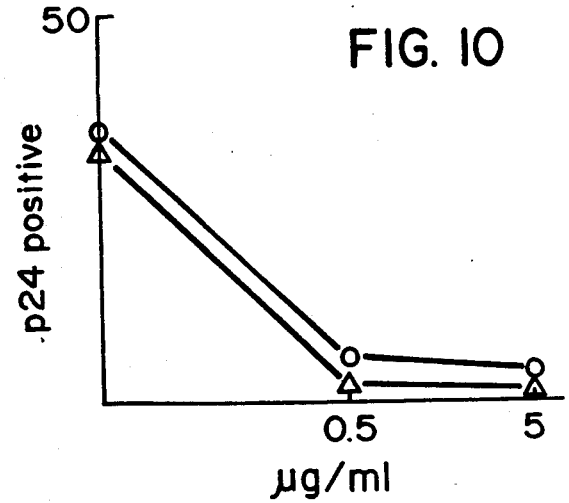

FIG. 5 shows the decrease in HIV replication in non-infected cells (open squares) and in infected cells treated with TCS and MMC demonstrated by decreased levels of particle associated reverse transcriptase detectable in the culture supernatant harvested 5 days after addition of TCS (solid diamonds) or MMC (solid squares);

FIGS. 6A and 6B are cytofluorographs of permeabilized uninfected (6A) and HIV-infected (6B) monocyte/macrophages after labeling with mouse anti-p24 antibody and fluorescent-tagged anti-mouse antibody;

FIG. 7 shows the increase in percent macrophages containing expressed viral p24 antigen, as a function of time after infection with HIV, in normal macrophages derived from each of two donors (open circles and triangles), and the change in cell viability which occurs in the cells during the same period (closed circles and triangles);

FIGS. 8A-8D are cytofluorographs of uninfected (8A) and HIV-infected (8B) monocyte/macrophages, and infected macrophages treated with 5 μg/ml of TCS (8C) or 5 μg/ml MMC (8D) four days prior to assaying for the presence of p24 viral antigen, as in FIG. 6;

FIG. 9 is a plot showing the change in percent HIV-infected monocyte/macrophage cells with threshhold levels of HIV p24 antigen, as measured at 0, 24, and 96 hours after exposure of the cells to 5 μg/ml of TCS (open triangles), MMC (open circles), or no drug treatment (solid circles);

FIG. 10 plots the change in percent HIV-infected monocyte/macrophage cells with threshhold levels of HIV p24 antigen, measured four days after exposure to 0, 0.5 or 5 μg/ml of TCS (open triangles) or MMC (open circles); and FIG. 11 is a plot showing the increase in HIV p24 antigen expression during a 10-day period after cells are first placed in culture (open squares), and the inhibition of p24 expression when the cells are exposed to 0.3 μg/ml TCS whe the cells are first placed in culture (closed circles) or when TCS (0.3 μg/ml) is added after 5 days in culture (closed squares), when a large proportion of the cultured cells are expressing p24 antigen.

Figure 12:
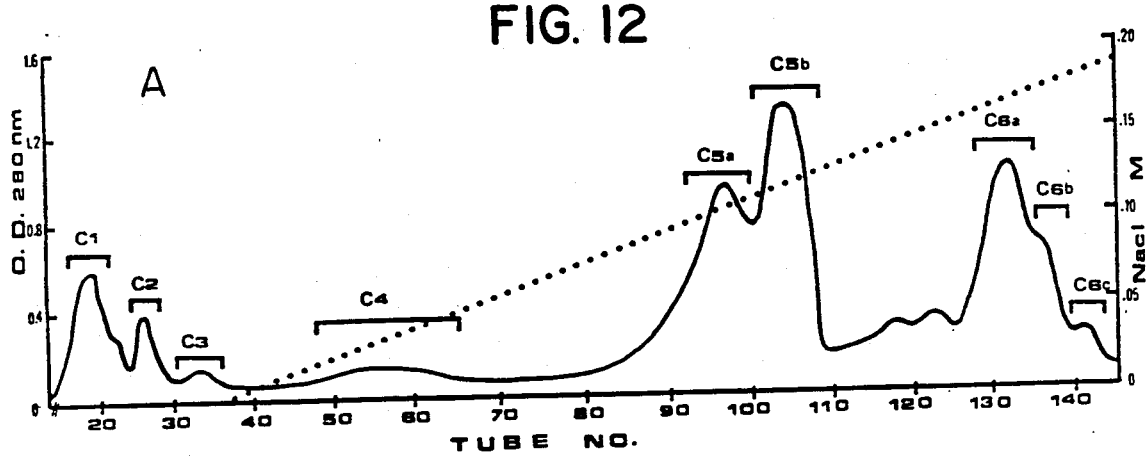
Figure 12:
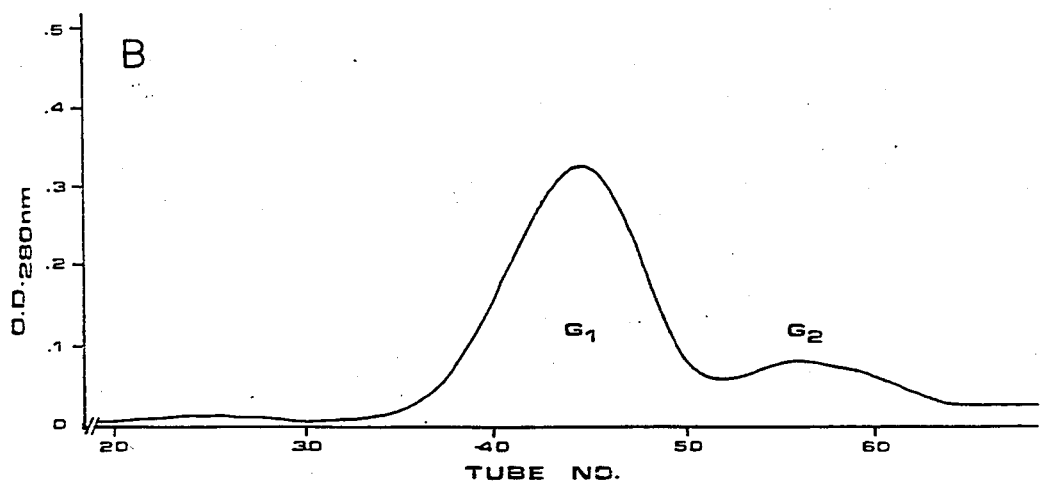
Figure 12:
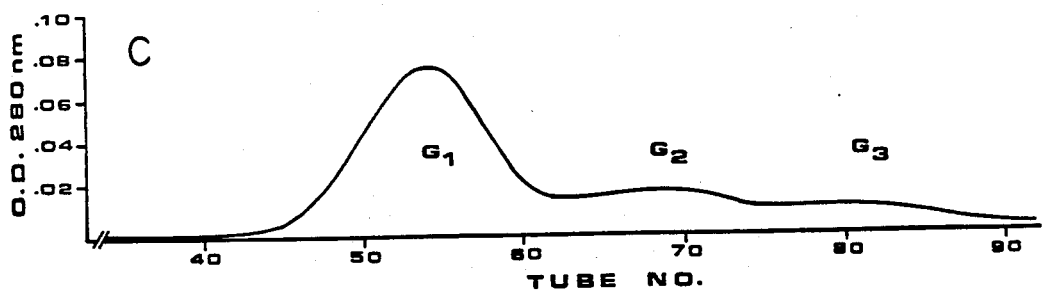
Figure 13:
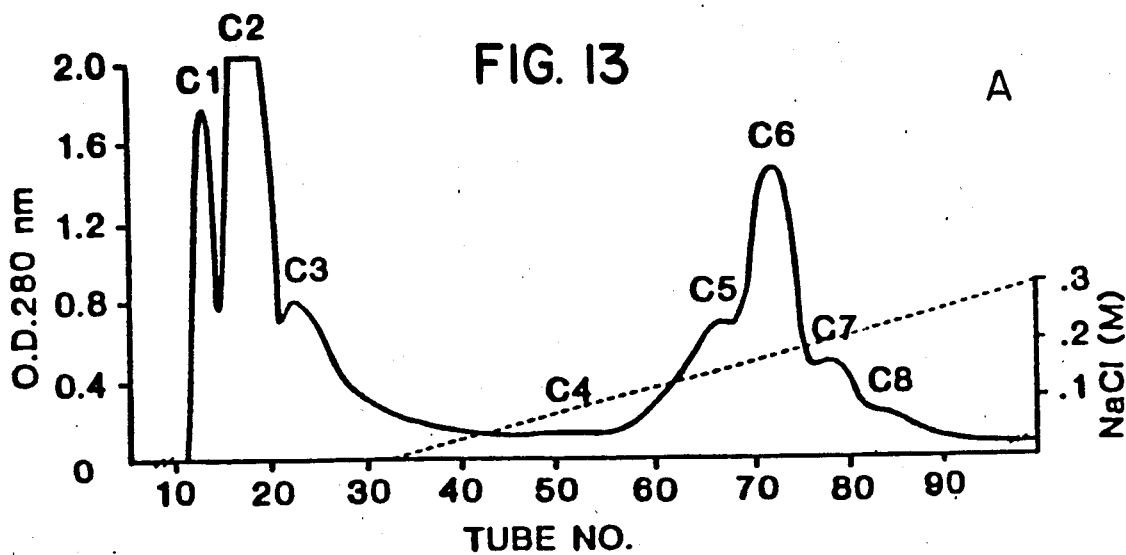
Figure 13:
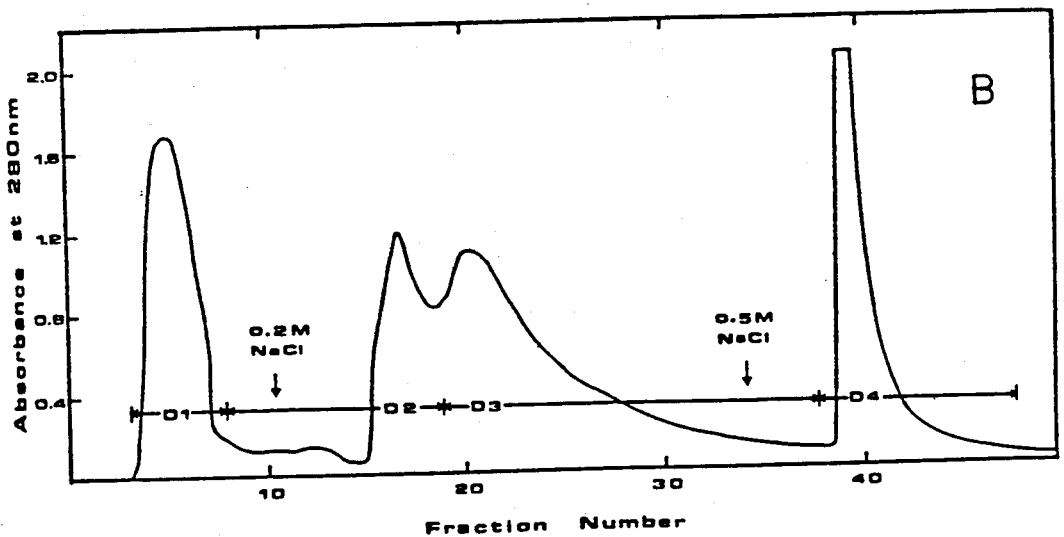
Figure 13:
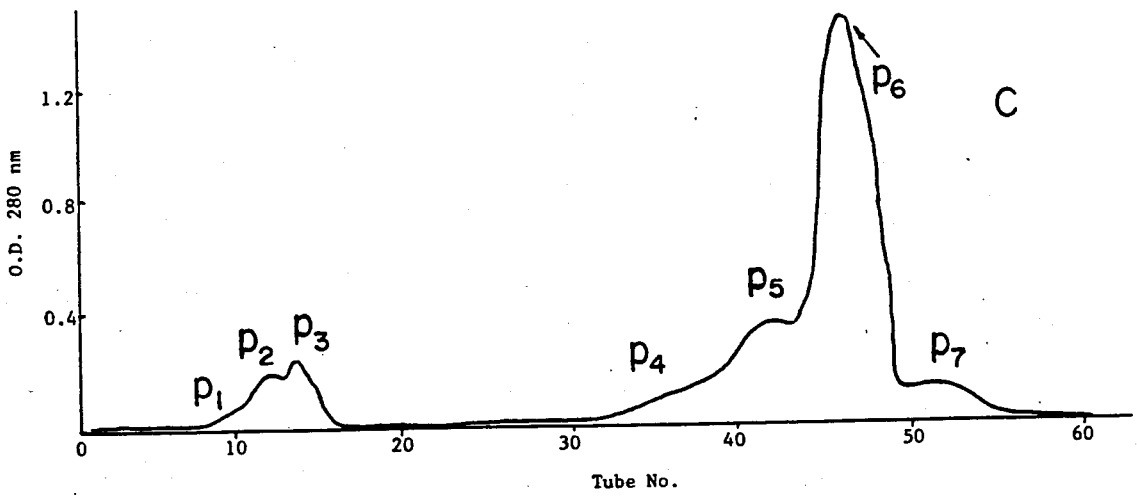

FIGS. 12A-12C show chromatography elution profiles obtained in the isolation of alpha and beta momorcharin, and FIGS. 13A-13C show chromatography elution profiles obtained in the isolation of trichosanthin.

DETAILED DESCRIPTION OF THE INVENTION

I. Anti-HIV Proteins

The plant proteins and glycoproteins described in this section have been identified, according to one aspect of the invention, by their ability to reduce HIV antigen expression in cultured, HIV-infected cells to background or near-background levels. Protein concentrations as low as 0.2-0.5 μg/ml are effective, and complete inhibition of viral antigen expression occurs within about 5-12 days. Concentrations between 0005 μg/ml and 0.5 are effective for inhibition of HIV-infected monocyte macrophages in vitro, and between 0.3 and 3 μg/ml, in HIV-infected T cells. The proteins are referred to collectively herein as anti-HIV proteins.

A. Trichosanthin

Trichosanthin (TCS) is a plant protein which is obtained from the *Trichosanthes kirilowii* root tuber. The protein, which is also known as alpha-trichosanthin (Law) and Rddix trichosanthis (Kuo-Fen), is a basic, single-chain protein consisting of between about 224 (Gu) to 234 (Xuejun) amino acid residues, and having a molecular weight of about 24,000 daltons. One preferred purification method for obtaining TCS in purified form is given in the Materials section. The protein sequence of TCS has been completed (Gu; Wang), and a molecular model has been derived from cytofluorographic X-ray analysis (Kezhen).

TCS, or plant extracts containing TCS, have been used in China as an abortifacient agent for inducing abortion in humans, particularly during midtrimester (14 to 26 weeks). As such, the drug has been administered by intramuscular, intravenous, or intraamniotic routes, typically at a single dose of between about 5–12 mg. The phenomenon of mid-term abortion has been attributed to the selective destruction of placental villi. Other studies indicate that the syncytiotrophoblast is preferentially affected (Hsu; Kao) and that secretion of hCG may be impaired (Xiong). Trichosanthin has also been shown to have a suppressive effect on human choriocarcinoma, and the protein appears to be able to pass the blood/brain barrier (Hwang). It has also been speculated, from the observed homology in amino acid sequence between trichosanthin and the A chain of Ricin, that the protein may have ribosome-inhibitory properties similar to ricin and various single-chain ribosome-inhibitor proteins, such as momorcharin, pokeweed anti-viral protein (PAP) wheat germ inhibitor, and gelonin (Xuejun).

As the term is defined herein, "trichosanthin" or "TCS" is intended to include the 24,000 dalton trichosanthin protein obtained as above, and modified proteins or peptides derived from natural trichosanthin which show the potent anti-HIV activity of natural trichosantin in HIV-infected cells, as characterized in Section II below.

B. Momorcharin

Morocharin (MMC) is a basic glycoprotein obtained from the seeds of the bitter melon plant *Momordica charantia*. The protein appears to have two related forms which have been designated alpha and beta momorcharin. Alpha-momorcharin has a reported molecular weight of between about 31,000 to 32,000 daltons and a neutral sugar content of about 1.6%. Beta-momorcharin has a reported molecular weight of about 29,000 daltons and a neutral sugar content of about 1.3% (Chan). Both forms of momorcharin are effective in inhibiting HIV antigen expression in HIV-infected T lymphocytes and monocyte/macrophages, according to the invention. Momorcharin is defined herein to include both alpha and beta momorcharin, as well as active portions of these proteins which are effective in inhibiting HIV antigen expression in HIV-infected blood cells.

Like trichosanthin, momorcharin has been studied heretofore for its ability to effect embryo implantation and produce early termination of pregnancy (Law, Chan). These studies indicate that both proteins inhibit embryonic implantation of mouse embryos by a similar mechanism, possibly involving reduction of trophoblast outgrowth and disrupting the development of inner cell mass. In mouse animal model studies, the proteins were both effective in terminating pregnancy when administered at a dose of about 0.2-0.3 µg/25 g animal weight.

The plant glycoprotein can be isolated to homogeneity by fractionating an acetone extract from the seeds of *M. charantia* on CM Sepharose CL-6B, and Sephadex G100, according to published methods (Yeung, 1985), and as detailed in the Methods section below. The protein is homogeneous on fractionation by SDS gel electrophoresis and immunoelectrophoresis.

Momorcharin appears to be related and perhaps even identical to one or more *M. charantia* inhibitors ("MCI") having molecular weights in the 30,000 to 32,000 dalton range, and possessing ribosome-inhibitory activity in cell-free systems. Such inhibitors which have been described in the literature are a *Momordica charantica* inhibitor, having molecular weights of 31,000 daltons (Falasca) or 30,000 daltons (Spreafico); "agglutinin", having a molecular weight of about 32,000 daltons (Lin); and possibly one or more of the four subunits (molecular weights 30,500, 29,000, 28,500 and 27,000 daltons) in a hemagglutinating lectin obtained from the seeds of *M. charantia* (Barbieri, 1980).

MCI is a potent inhibitor of protein synthesis in cell-free system, but is much less toxic to intact cells than ribosome inhibitor proteins, such as ricin, which have a second subunit which facilitates uptake of the toxin by cells (Barbieri). It is noted that the MCI which has been most extensively studied as a ribosome inhibitor protein was originally characterized as a 23,000 dalton protein, although a subsequent molecular weight determination yielded a molecular weight of about 31,000 daltons (Falasca).

II. Inhibition of HIV Antigen Expression

Figure 4:
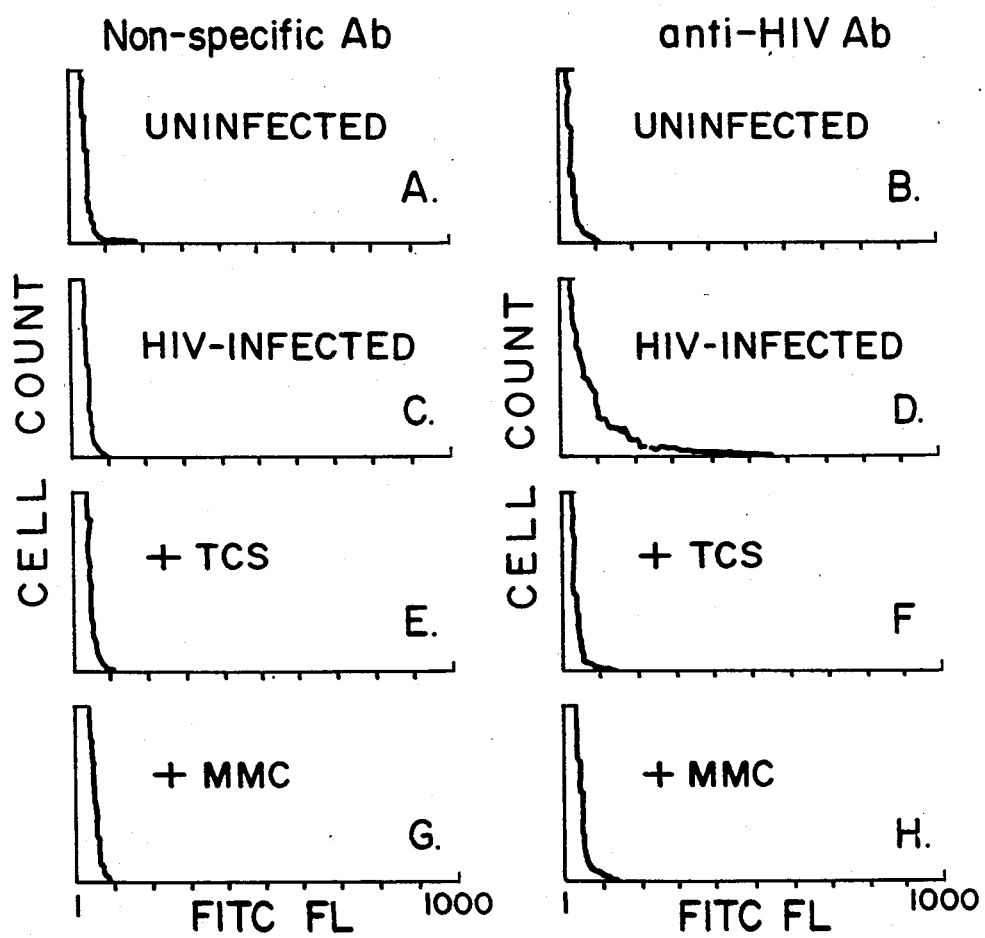
FIGS. 4A–4H are cytofluorographic plots (linear scale) of T cells reacted first with control (non-specific)

This section outlines methods for culturing human mononuclear cells which are (a) infectable or infected by HIV, and (b) show a dramatic reduction in HIV antigen expression when treated with low doses of one of the above anti-HIV proteins. The two blood cell types which are specifically described are cells of T lymphoid lineage (T cells), whose destruction in vivo is associated with loss of immunological function in advanced clinical HIV infection; and monocyte/macrophages, which likely provide a reservoir of the virus in the infected individual, may, when expressing HIV proteins, be capable of fusing with and destroying T cells, and may also play a role in the spread of the infection, such as within the nervous system (Koenig).

A. T Lymphocytes

Normal human T lymphocytes can be prepared from peripheral blood or from human spleen biopsies by standard procedures (Foung). The cells include a fraction of CD4+ cells which may be further isolated, if desired, by affinity methods which are specific for the CD4+ surface antigen (Wysocki). In the usual case, the mixture of CD4+ and nonCD4+ cells are employed. The cells are maintained in culture over a several-day to several-week period by activation with a known lymphocyte mitogen, such as PHA, and in standard cell media, such as RPMI-1640 medium supplemented with fetal calf serum and interleukin-2. The cultured T lymphocytes may be infected with HIV in vitro, e.g., using an HIV isolate derived from an AIDS patient.

Alternatively, the T lymphocyte cells may be leukemic cells derived from a human patient with T-cell lymphoma (Lifson, 1986a, 1986b; Popovic). Here the cells are cultured directly (without a requrrement for activation) in a standard medium, like that used above.

In the methods reported in Examples 1–3, the cultured T lymphocytes employed were derived from the H9 cell line (Popovic) and were chronically infected in vitro with the well characterized HIV isolate HXB-2 (Fisher).

The effect of TCS and MMC on cell viability of infected and non-infected T lymphocytes (H9 cell line) was examined at TCS and MMC concentrations between about 0.3 and 30 μg/ml in the culture medium, as detailed in Example 1A. Viable cell numbers, 2 and 5 days following exposure to TCS at the concentration indicated, are plotted in FIGS. 1A and 1B, respectively, and percent viable cells, in FIG. 1C where cell viability was determined by dye exclusion.

The cell viability data in FIG. 1 shows that infected cells are more susceptible to killing, particularly at higher concentrations of TCS, with a more pronounced effect observed at 2 days than at 5 days. This likely reflects the fact that less than one hundred percent of the cells within the "infected" population were actually productively infected. Cells which are not productively infected appear to be less susceptible to TCS and MMC; the apparent relatively lesser effect of drug exposure on cell counts at day 5 may reflect preferential outgrowth of individual cells within the "infected" population which were not themselves productively infected. Comparison of total viable cell numbers with percentage viability suggests that TCS, in a dose-dependent fashion, can exert both cytocidal (cell killing) and cytostatic (cell growth inhibiting) effects, with preferential effects at a given peptide concentration on HIV infected cells relative to uninfected cells. Similar results were obtained with alpha and beta-MMC.

The effects of TCS and alpha-MMC on cellular proliferation, as assessed by measuring incorporation of [$^3$H]-thymidine into DNA, were studied after a 2 day treatment of HIV infected and uninfected Tccells with varying concentrations of the peptides. As shown in FIG. 2, TCS and alpha-MMC produced a concentration dependent inhibition of [$^3$H]-thymidine incorporation, with a preferential effect on HIV infected cells. When the effects of these and similar agents on protein synthesis were studied by measuring incorporation of [$^3$H]-leucine into labeled, trichloroacetic acid precipitable material, concentration dependent inhibition of protein synthesis by HIV infected cells was observed (FIG. 3). Details of these studies are given in Examples 1B and 1C.

One characteristic of HIV-infected T cells is the appearance of HIV envelope proteins, particularly the major envelope proteins gp120 and gp41, on the surface of the infected cells. As indicated above, gp120 appears to play a critical role in the recognition of CD4+ T lymphocytes, and the subsequent destruction of these lymphocytes. gp41 may also participate in HIV envelope mediated cell fusion (Kennedy). Therefore, the ability of the anti-HIV proteins herein to inhibit expression of these viral antigens may be an important indicator of the ability of the protein to inhibit virally mediated processes leading to T cell destruction and to arrest the loss of immunological function seen in HIV-related diseases, such as AIDS.

The effects of TCS and alpha-MMC on the expression of HIV antigens (including gp120 and gp41) on the surface of infected cells were thus studied. The results of TCS and MMC treatment on HIV antigen expressio are shown in FIG. 4. HIV infected T cells (H9 cell line) were treated with 10 μg/ml of TCS or alpha-MMC for 16 days, then tested for HIV antigen expression by indirect immunofluorescence analysis. Briefly, human serum was incubated with test cells, followed by washing and detection of bound specific IgG with a fluoresceinated goat anti-human IgG reagent, as detailed in Example 2. As shown in FIG. 4, treatment of HIV infected cells with TCS and alpha-MMC reduced HIV antigen expression to undetectable levels.

Figure 1:
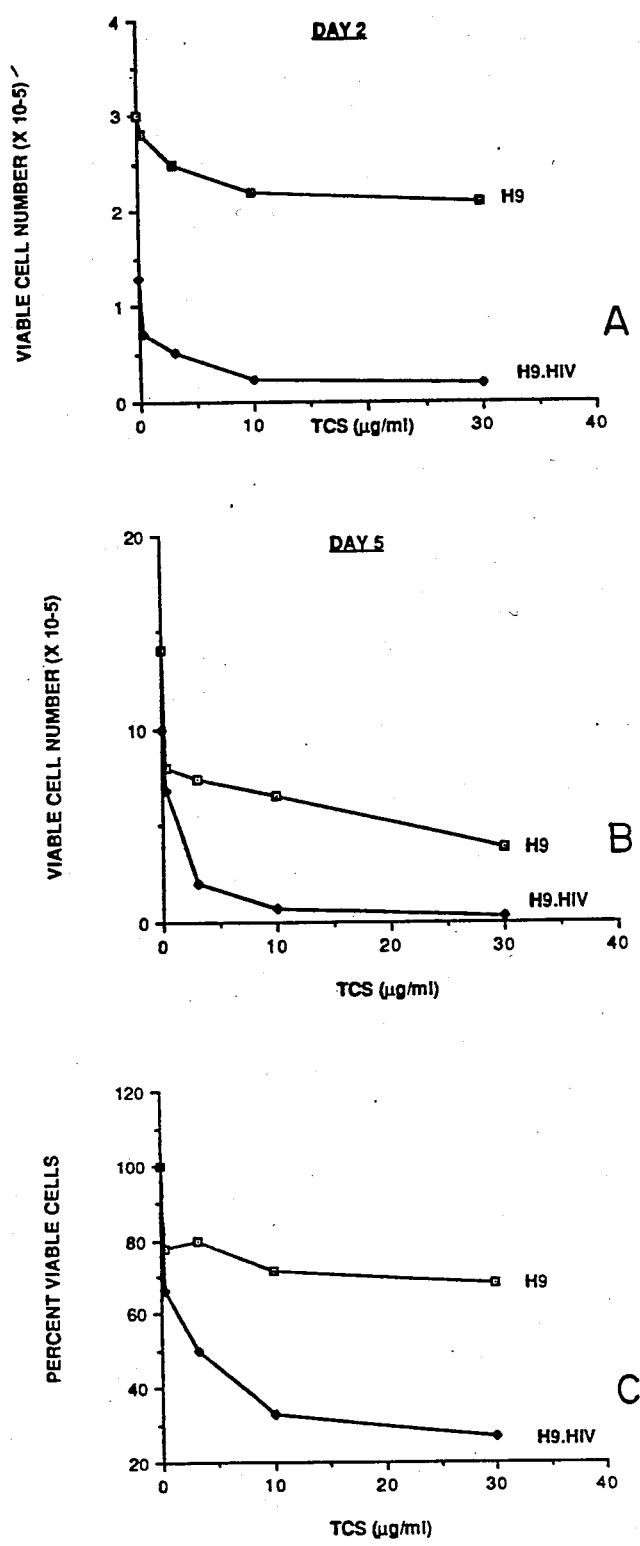
FIGS. 1A and 1B are plots which depict the absolute viable cell counts for identically seeded cultures of HIV infected and uniffected T lymphoid cells cultured in the presence of varying concentrations of TCS for 2 days (FIG. 1A) or 5 days (FIG. 1B)
FIG. 1C shows the percentage of viable cells present after 2 days in identically seeded cultures treated with varying concentrations of TCS.

The results demonstrate that both anti-viral proteins are able to effectively eliminate the expression of viral antigens (including the pathogenically significant antigens gp120 and gp41) on the surface of HIV-infected T lymphoid cells, and that this inhibition can be achieved at concentrations of anti-viral protein at which uninfected cells are largely unaffected, and only a portion of infected cells are killed (FIGS. 1 and 4).

To assess the ability of the anti-viral proteins to inhibit viral replication in HIV infected cells, the level of particle associated reverse transcriptase (RT) activity present in cell free culture supernatants was measured. RT activity was determined as detailed in Example 3. As shown in FIG. 5, treatment of infected cells with TCS or alpha-MMC resulted in a virtually complete inhibition of viral replication. RT activity in supernatants of treated cultures was reduced to essentially background levels 5 days following treatment with the highest concentration of TCS, with a substantial reduction observed following treatment with alpha-MMC as well.

B. Monocyte/Macrophages

Monocyte/macrophages are the macrophage-lineage cells present in the peripheral blood which are precursors of tissue macrophages. These cells, which will be referred to herein for simplicity as "monocytes", can be isolated from peripheral blood or from human spleen biopsies by known procedures (Crowe). The cells are preferably cultured in a novel in vitro culture system which employs Teflon® coated culture vessels, as described in Example 4A. Upon in vitro culture, peripheral blood derived monocytes undergo differentiation, acquiring some characteristics of tissue macrophages. For isolation of monocyte/macrophages, peripheral blood mononuclear cells are allowed to attach to a glass dish, permitting separation of the monocytes from non-adherent lymphocytes. The separated monocytes are then cultured as a suspension on Teflon®-coated dishes. The cells can be maintained in a viable state in culture for up to four months or more without signicant loss of cell viability.

The cells can be infected in vitro with an HIV isolate, as described in Example 4, or obtained in infected form from an HIV-infected individual, by similar methods. Before describing the effect of viral infection on cell viability and viral antigen expression, it is worth mentioning how viral antigen expression can be measured readily. Although it is possible to measure viral envelope protein on the cell surface, as was done for T lymphocytes, this method has the limitation that the monocyte/macrophages are cultured in the presence of human serum. Serum derived immunoglobulin may be passively and non-specifically absorbed to the surfaces of the cells, for example, via the Fc receptor. This non-specifically bound Ig would be detected along with anti-HIV antibody used to detect infection when reacted with fluorescent-labeled anti-human IgG antibody reagent. To avoid this problem, the cells may be assayed for a viral protein, such as HIV core protein p24, which is localized predominantly within the infected eells. p24 has the added advantage that a mouse monoclonal antibody specific against the ntigen is available. In the assay method, the cells are reacted with the anti-p24 antibody after treatment with a membrane-permeabilizing agent, such as Triton X-100® which facilitates entry of the antibody through the cell membrane, then treated with a fluorescent-tagged anti-mouse IgG antibody to detect antibody bound to the viral antigen. The cells are then subjected to quantitative flow cytometric analysis. These methods are detailed in Example 4. FIGS. 6A and 6B show cytofluorographs of HIV-infected monocytes reacted with control (non-specific) or mouse anti-p24 antibodies, respectively, measured 10 days after HIV infection in vitro. About 60% of the cells have above threshhold fluorescence, indicating HIV infection.

One important feature of the monocyte cell culture system, for studying HIV infection and inhibitors, is that the cells can be maintained in an actively infected state in culture for extended periods of several weeks or more. This faature is seen in FIG. 7, which plots monocyte viability (closed symbols) and p24 antigen levels (open symbols as a function of days after infection in vitro with HIV, where the circles and triangles represent two different mooocyte donors. Experimental details are given in Example 4. As seen, viral antigen increases steadily to a maximum of about 50-60% infected cells, then plateaus after about two weeks, while cell viability remains substantially unchanged over the test period.

Figure 8:
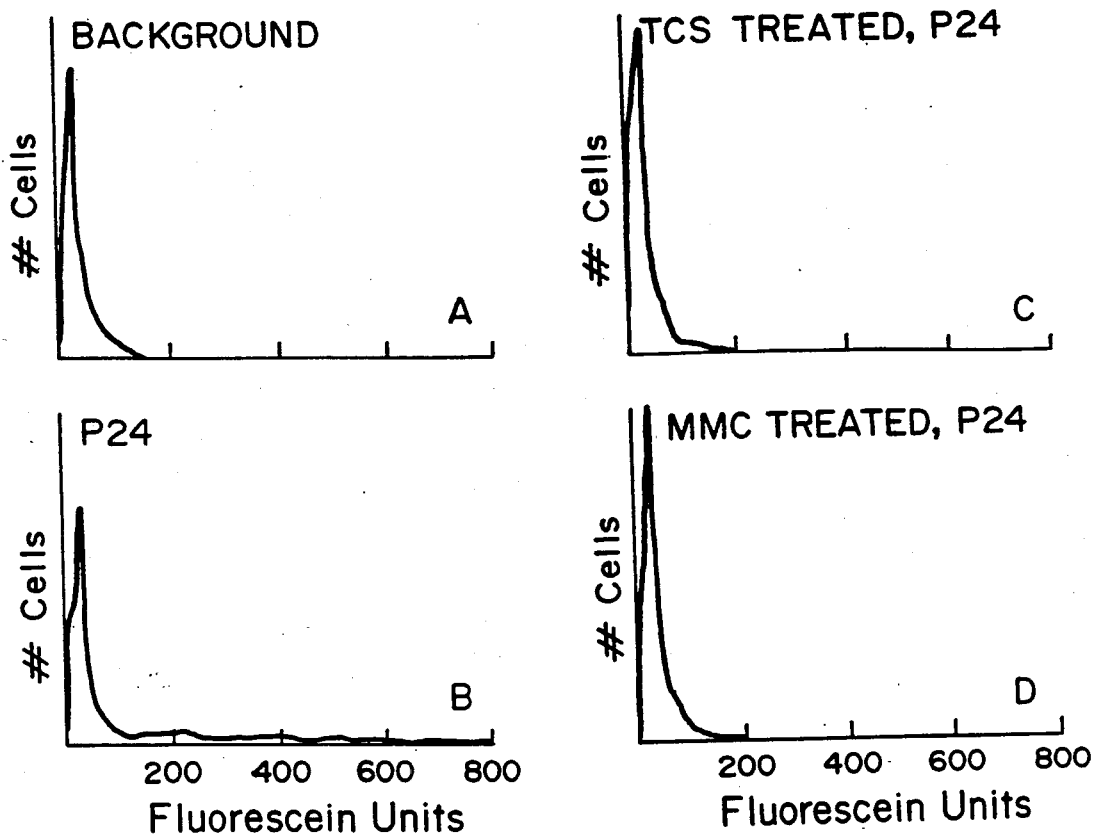

The rapid and substantially complete inhibition of viral antigen expression in HIV-infected monocytes, when expoeed to TCS or MMC, is illustrated in FIG. 8. Here, monocytes were exposed to 5 $\mu$g/ml TCS or MMC ten days after HIV infection, and four days later, the cells were assayed by fluorocytometry. FIGS. 8A and 8B show the fluorocytographs of untreated cells analyzed after reaction with control (non-specific) and anti-p24 antibody, similar to FIGS. 6A and 6B, respectively. The fluorocytographs of TCS- and MMC-treated cells are shown in FIGS. 8C and 8D, respectively. The level of p24 seen in the protein-treated cells is close to background (FIG. 8A), indicating substantially complete inhibition of viral antigen expression four days after cell exposure to anti-viral proteins. Example 6 gives details of the method.

The time course of loss of p24 antigen in infected monocytes after exposure to TCS or MMC can be seen in FIG. 9. Each time point represents percent cells with an above-background antigen-specific fluorescence, determined as above by fluorocytometry. Untreated cells (solid circles) show little change in antigen levels, whereas both TCS (triangles) and MMC (open circles) treated cells show a severalfold reduction in viral antigens 1 day after, and substantially complete loss of p24 antigen 4 days after exposure to TCS or MMC. Details of the study are given in Example 7.

To determine a lower effective dose range of TCS and MMC, infected monocytes were treated with 0.5 or 5 $\mu$g/ml of the anti-viral protein, and assayed for p24 expression and cell viability 4 days after exposure to the drug. FIG. 10 shows the inhibition of p24 antigen at the two concentrations of TCS (triangles) and MMC (open circles). Potent inhibition of viral antigen expression 4 days after exposure to TCS or MMC was seen at both concentrations.

Taken together, the results just discussed show that both TCS and MMC can effect substantially complete inhibition of HIV antigen expression in infected monocytes, at concentrations that produce only a slight reduction in cell viability. Loss of viral antigen appears complete within about 4 days of cell exposure to the anti-viral proteins.

The presence of HIV in macrophages isolated from AIDS patients, and the inhibition of HIV antigen expression in "preinfected" monocytes was also examined. Several monocyte preparations from both peripheral blood and spleen cells from AIDS patients were tested for p24 antigen expression. The macrophage cultures were established essentially as described in Example 4, except that the donors were HIV seropositive, and no exogenous virus was added to accomplish in vitro infection. The source of HIV in the culture was that present from natural, in vivo infection of the cell donor. Monocytes tested immediately after isolation contained only a small prrcentage of HIV positive cells, as evidenced by the presence of p24 antigen. The percentage of cells expressing p24 increased gradually over a 3 to 4 day period in culture, as indicated for a culture of spleen monoyytes (open squares) in FIG. 11. In five different monocyte preparations derived from HIV-seroposttive individuals which have been examined, the cultured cells expressed between about 10%-40% p24 after 3-4 days in culture. The results indicate that a high proportion of monocytes present in HIV seropositive individuals are infected with HIV. Apparently only a small percentage of those infected cells express HIV antigens unless cultured for short periods in vitro. The possibility that the increase in number of cells expression p24 is caused by the spread of the virus among the cultured cells is unlikely, given the relatively slow rate of p24 expression in newly-infected cultured monocytes (FIG. 7).

The inhibitory effect of TCS on p24 expression in the in vivo infected cells was examined both at the initiation of the culture, when the percentage of p24 expressing cells was quite low and, in a separate culture, 5 days after initiation of culture, at which time p24 expression was observed in about 45% of the cells. FIG. 11 shows the results of TCS treatment (0.3 μg/ml) of $5 \times 10^5$ monocytes cultured over a ten day period. TCS added at the initiation of the culture completely prevented HIV antigen expression over the 10-day test period. When added to the 5-day monocyte culture, TCS reduced the percentage of cells expressing p24 from about 45% to 2% within three days, and further reduced the percent antigen-expressing cells to background level within 5 days. It is clear from the data that TCS can block HIV antigen expression in monocytes derived from an infected individual, either before or after antigen expression occurs in culture.

III. Treating HIV Infection in Humans

One of the crucial events in the etiology of AIDS appears to be the destruction of CD4+ T lymphocytes, and there is in vitro and in vivo evidence to suggest that at least one mechanism of cell destruction involves fusion of infected cells to form large multi-nucleate cells. The inventors and their co-workers have previously studied the relationship between expression of the CD4 antigen and infectability by HIV (Lifson, 1986a, 1986b, 1986c). The studies confirmed earlier reports that HIV infection of T lymphocytes requires the CD4 antigen, suggesting that a critical event in the infection process involves interactions between the CD4 antigen and one or more envelope proteins of HIV (Dalgleish; Klatzman, 1984a, 1984b; McDougal, 1985a, 1985b, 1986; and Maddon, Sodroski). The previous study by the inventors also showed that infected T cells can fuse with both infected and non-infected CD4+ T cells in vitro to produce large multi-nucleate syncitia, and that cell fusion can be blocked with addition of antiCD4 antibodies. This indicates that cell fusion, like HIV infection, requires interactions between viral antigens on the surface of infected cells and the T lymphocyte CD4 antigen (in either infected or non-infected cells). The result may also explain how a large portion of CD4+ T cells can be destroyed in vivo, even though only a relatively small number of isolated CD4+ T cells from an HIV-infected individual show evidence of HIV infection. According to this mechanism, infected T lymphocytes would "recruit" healthy T cells for cell fusion and destruction.

Using T lymphocytes which had been selected for high CD4+ antigen expression, the inventors have further shown in previous studies that (a) the infectability of the T lymphocytes with HIV increases substantially with increased surface concentration of the antigen, and (b) syncytia formation due to cell fusion is much more rapid in the high CD4+cells. The results support earlier findings on the importance of the CD4+ antigen in HIV infection and subsequent cell-fusion events. It is also noted that the high-CD4+ cells, which can be readily selected by fluorescence cell sorting, are potentially useful in a more rapid and sensitive CPE assay for HIV.

There is also evidence that monocyte/macrophages may be involved the etiology of HIV infection. It has been reported that cells of the monocyte/macrophage lineage can be infected with HIV in vitro (Crowe, 1987; Gartner, 1986a, 1986b; Koenig; Ho; Chayt; Armstrong; Steicher), and monocytes have been implicated in the spread of HIV into theccentral nervous sytem (Koenig). The studies reported above on monocytes prepared from HIV-infected patients indicate that a large percentage of blood and splenic macrophages may harbor HIV infection, even though viral antigens may be actively expressed in vivo in a relatively small percentage of the cells. In addition to providing a possible reservoir of HIV in the body, macrophages may also be directly involved in the destruction of T lymphocytes by cell fusion. Recent studies by the inventors and their co-workers show that HIV-infected monocytes are capable of fusing readily with non-infected CD4+ lymphocytes, forming giant multi-nucleate syncytia (Crowe). There is also evidence of macrophage involvement in HIV infection of the CNS (Koenig).

It can be appreciated from the foregoing how the viral inhibition effects produced by the above anti-HIV proteins are useful in treating humans infected with HIV. First, the ability of the proteins to inhibit viral replication in infected cells, as evidenced by the sharp decline in reverse transcriptase activity associated with the cells, would reduce the level of infection by reducing the production of new virus capable of infecting new cells. In addition, inhibition of viral replication may help to eliminate the virus "reservoir" which may be provided by the monocyte/macrophages and other cells. In this regard, it is noted that TCS appears to be able to cross the blood/brain barrier (Hwang) and thus should be effective against the spread of HIV infection to the CNS.

Secondly, the evidence above suggests that the fusion of CD4+ T cells with infected T cells or monocyte/-macrophages requires the presence of HIV antigens, likely including the gp120 antigen, on the surface of the infected cells. One striking effect of the anti-HIV proteins is the ability to inhibit and substantially eliminate expression of viral antigens, such as gp120, in infected cells. Substantial reduction in the expression of viral proteins wolld be expected to be associated with a marked reduction in the cytopathogenic consequences of infection.

The anti-HIV proteins can also be expected to inhibit or prevent other events related to the loss of immunological competence in HIV infected individuals, through general suppression of virus levels and inhibition of viral protein synthesis in infected cells. For example, by inhibiting HIV antigen expression and/or reverse transcription levels in infected lymphocytes. The anti-HIV agents may be effective against B-cell lymphoma, one of the most serious and rapidly fatal clinical manifestations of HIV infection.

At the same time, the behavior of the cells in vitro indicates that the levels of anti-HIV protein which are effective in preventing viral antigen production are only slightly cytotoxic to non-infected blood cells, and effective to selectively reduce the number of infected cells relative to non-infected cells of the same type. Effective levels of both TCS and MMC are in the range of about 0.5 to 3 $\mu$g/ml cell suspension, depending on cell type. These levels can be achieved in the plasma, assuming an approximately five liter blood volume, by administering betwenn about 1.5 to 15 mg of the anti-HIV protein per dose. This drug dose corresponds roughly to the 5-12.5 mg dose of TCS which is used for inducing abortion in humans, and this dosage level is not generally associated with serious side effects in humans (Kuo-Feng; Hwang).

The protein may be administered parenterally in one of a variety of delivery forms, including solution form, lipsome-encapsulaeed form, and attached to a carrier, such as an anti-T cell, anti-macrophage, or anti-HIV antibody, for targeting the protein to HIV-infectable or infected cells. Methods for preparing and storing peptide drug formulations of various types, and for administering the formulation by intravenous, intramuscular, subcutaneous, mucosal membrane, and inhalation routes are well known in the pharmaceutical industry. It is noted here only that some delivery forms, such as intramuscllar placement of liposome-encapsulate protein, or protein enmeshed in a collagen matrix, will provide slow release of the drug into the bloodstream, providing redueed toxicity and the possibility of greater viral inhibition.

In a typical treatment regimen, the drug is initially administered at a selected dose, and the effectiveness of the first dose is assayed, within several days of protein administration, for inhibition of HIV antigens in isolated blood cells. Preferably, either T lymphocytes or monocyte/macrophage cells are prepared and cultured as above, before and after protein administration, and the extent of viral antigen production is assayed as above. HIV p24 antigen present in the plasma of some infected patients can also be monitored as a parameter measuring in vivo viral replication. The effects of administration of the proteins on plasma p24 levels can be readily followed using an ELISA procedure. The course of the treatment may be followed over a several week period with additional viral antigen assays of isolated blood samples. Additional protein is administered as needed to effect substantial reduction in viral antigen expression in infected blood cells or in plasma p24 levels, consistent with avoiding cumulative dose levels which give serious loss of cell viability and toxicity effects.

When a series of doses are administered, e.g., over several-week period, the patient should be monitored for allergic response to the anti-HIV protein. If a serious response does develop to the first-administered drug, e.g., TC,, a second drug, e.g., MMC, can be administered to minimize immunological reaction and neutralization of the protein. Preliminary animal data developed by one of the inventors suggest tha the two proteins are substantially immunologically non-cross reactive. However, since many patients receiving the treatment are seriously immune compromised, immune response to the proteins may be a relatively minor side effect.

IV. Screening Compounds for Anti-HIV Activity

The studies described in Section II above demonstrate that cultured, HIV-infected blood cells, such as T lymphocytes and monocyte/macrophages, can provide a rapid and sensitive response to compounds which re effective as inhibitors of HIV infection. In particular, the inhibition of viral antigens in the cells may be an important indicator of a test compound's abiltty to suppress the fusion of HIV-infected cells with CD4+ T cells, a process that requires the eppression of viral antigens on the surface of the infected cells, as discussed above. Other sessitive indicators of anti-HIV activity in the infected cells include inhibitio of measured reverse transcriptase activity and viral core protein (p24) present in the supernatants of treated culture. Decreases in these measured paramaters parallel the sharp drop in viral antigen eppression in the treated cells.

In the drug screening method of the invention, HIV susceptible cells, such as T lymphocytes or monocyte/macrophages are prepared for culture, as described above and in Examples 1 and 4. The cells may be infected in vitro as described, or obtained from an in vivo infected HIV-seropositive individual. In either case, the cells are preferably cultured in vitro for a period sufficient to allow for stabilization of the observed levels of viral antigens in the infected cells, before attempting treatment of the infected cultures with test compounds. In the case of monocyte/macrophages infected in vitro, the antigen-stabilization period is typically about 2 weeks (FIG. 7). Where these cells are derived from an infected individual, a culture period of 3-4 days is sufficient (FIG. 11).

When stable levels of antigen expression in the cultured cells are established, the cells are exposed to a selected test compound, typically at increasing concentrations of the compound, which are within acceptable in vivo concentrations, as judged either by drug toxicity concentrations or LD$_{50}$ values, if known, or by cell viability in control (non-infected) cells exposed to the selected concentrations of the drug. At suitable times following exposure, typically between about 1-5 days, the cells are assayed for level of viral antigen expression. The results with TCS and MMC suggest that nearly complete inhibition of viral antigen expression can be expected in monocyte/macrophages at low concentrations of effective anti-HIV compounds, preferably concentrations which do not affect the viability of non-infected cells.

Compounds which are identified as potent inhibitors of viral antigen expression can, as above, be further characterized for cell toxicity, to determine whether inhibitory doses of the compound are reasonably non-toxic to uninfected cells. The effect of the compoudd on p24 antigen expression and reverse transcriptase activity associated with the infected culture provides additional information about the ability of the compound to inhibit viral replication and infectivity.

The monocyte/macrophage screening system used in Section II indicates the types of cell response which can be expected for effective anti-HIV compounds:

(a) the compounds produce nearly complete inhibition of viral antigens within several days of exposure to the test compound;

(b) the effective dose levels are not highly toxic to uninfected cells, as evidenced by very little change in cell viability; and (c) reverse transcriptase activity and p24 production associated with the infected cells are markedly reduced.

By these criteria, both TCS add alpha and beta MMC have been identified herein as effective anti-HIV compounds.

A number of other compounds have also been screened, according to the present method, for anti-HIV activity in the monocyte/mccrophage system. Four of these compounds, which have been demonstrated by others to have some anti-HIV activity when assayed using T cells (Yarochan, 1986, 1987; McCormick), were tested. These were: ribavarin, phosphonoformate, phosphonoacetate, and azidothymidine (AZT), at the concentrations indicated in Table 1 of Example 5. As seen from the results in Table 1, none of the compounds, even at relatively high (and moderately toxic) concentrations were effective in reducing viral antigen expression to background levels, except in the case of 300 µg/ml phosphonoformate, where control antigen llevel was quite low (14% of the cells). Based on the criteria indicated above, this set of four drugs would not be identified as effective anti-HIV compounds in the monocyte/macrophage screening systems.

Plant and bacterial cytotoxins offer another class of compounds which could be profitably screened for anti-HIV activity, according to the above criteria. Several plant cytotoxins have been identified as ribosome inhibitor proteins, and possibly have crucial mechanism(s) of protein systhesis inhibition in common with TCS and/or MMC. Other plant and bacterial cytotoxins not specifically identified as ribosome inhibitors may also have protein inhibitory effects which could selectively inhibit expression of HIV antigens in infected cells. Some specific cytotoxins suggested for screening are:

1. Isolectins from *Trichosanthes kirilowii*. Three isolectins isolated from an acetone extract from *T. kirilowii* have been reported (Yeung). The lectins all have phytohemagglutinating activity, but unlike trichosanthin, do not exhibit abortifacient activity.

2. Cytostatic factor (11,000 daltons) from *Momordica charantia*. This factor inhibits protein synthesis in tissue culture cells, and is preferentially cytostatic for human leukemic lymphocytes when compared with normal peripheral blood lymphocytes (Takemoto, 1982). The cited reference describes purification and physical characterization of the factor.

3. Cytostatic factor (40,000 daltons) from *Momordica charantia*. The factor inhibits both RNA and DNA synthesis in intact tissue culture cells, and inhibits protein synthesis in a cell-free wheat germ system. The purified factor is cytostatic for leukemic cell lines, and has anti-viral activity against vesiclar stomatitis virus (VSV) in infected BHK-21 cells, as evidenced by inhibition of plaque-forming ability (Takemoto, 1983a).

4. Hemagglutinating lectin (115,000 daltons) from *Momordica charantia*. This lectin, which consists of four subunits of molecular weights 30,500, 29,000, 28,500, and 27,000, is a hemagglutinating lectin which is inhibited by galactose, galactose-containing sugars, and alpha and beta methylglucose. The factor inhibits protein synthesis in a cell-free protein synthesizing system, and partially inhibits protein synthesis in Yoshida ascites cells at a concentration of about 100 µg/ml (Barbieri, 1980).

5. Agglutinin, a 32,000 dalton lectin from *Momordica charantia*. The lectin agglutinates erythrocytes, and inhibits protein synthesis in Ehrlich ascites cells, at relatively high concentrations (Lin).

6. Momordin, a 24,000 dalton lectin from *Momordica charantia*. Like agglutinin, this factor agglutinates erythrocytes, and inhibits protein synthesis in Ehrlich ascites cells, at relatively high concentrations (Lin).

7. *Momordica charantia* inhibitor (MCI). This protein has been characterized variously as having a molecular weight of about 23,000 daltons (Barbieri), 30,000 daltons (Spreafico), and 31,000 (Falasca). The factor appears to be a ribosome inactivating protein characterized by potent inhibition of protein synthesis by cell-free systems, with little effect on intact cells (Falasca). Like the phytohemagglutinating protein from the same source, the factor inhibits DNA synthesis and protein synthesis in PHA-stimulated lymphocytes, and at concentrations much lower than those required to inhibit protein synthesis in Yoshida ascites cells (Licastro). The protein possesses potent immunomodulatory activity, as evidenced by inhibition of lymphoid cell responsiveness to PHA and ConA, and markedly enhanced macrophage-dependent cytotoxicity (Spreafico). MCI has reported anti-viral activity against herpes simplex virus-1 (HSV-1) and polio virus I in infected HEp-2 cells, as evidenced by reduced viral yield, and decreased plaque-forming ability (Foa-Tomasi). Concentrations of the compound giving significant viral inhibition were 100–200 µg/ml.

8. Gelonin, dianthin 30, dianthin 32, and pokeweed antiviral protein (PAP and PAP-S). Gelonin (Stirpe, 1980), dianthins (Stirpe, 1981), PAP and PAP-S (Barbieri, 1982; Irvin) can be purified as described in the respective references. Like MCI, these proteins are all singlechain ribosome inactivating proteins and appear to act through a mechanism involving inactivation of eukaryotic ribosomes (Falasca, Xeujun). PAP-S gives immunomodulatory effects similar to those observed with MCI (Spreafico). Gelonin, PAP-S, and dianthin 32, similar to MCI, all show anti-viral effects against HSV-I and polio virus I infected HEp-2 cells, as evidenced by reduced viral yields and decreased HSV-1 plaque-forming ability, at inhibitor concentrations of 100 or 200 µg/ml (Foa-Tomasi). It is noted that the inhibition of viral yields were relatively modest (31–90 percent inhibition of plaque-forming units), even at the high inhibitor concentrations used.

9. Wheat germ inhibitor. This protein appears to to resemble other single chain ribosome inhibitors in its ability to act as a potent inhibitor of in vitro protein synthesis, and its relatively weak inhibitory effect on many intact cells (Roberts).

10. Ricin, abrin, and modecin. These are two-subunit plant lectins which are potent inhibitors of protein synthesis in cell-free sytstems, and also are highly toxic to cells and animals, presumably because of their ability to penetrate cell membrane readily. The test material would include both the ribosome inhibitor subunit A alone, and the complete two-subunit molecule. As indicated above, sequence analogy between trichosanthin and the A subunit of ricin suggests the possibility of a common mechanism of ribosome inhibition (Xuejun). Ricin and abrin are reviewed by Olsnes, and modecin, by Gasperi-Campani.

11. Various hemagglutinating lectins, including agglutinin from *Ricinus communis* (Saltvedt), *Crotalaria juncea* lectin, *Vicia cracca* lectin, *Rutilis rutilus* lectin (Barbieri, 1979, 1980), and *Bandeiraea simplicifolia* lectin (Stanley). These lectins all inhibit protein synthesis in cell-free systems, but are inhibitory to intact cells only at relatively high concentrations.

12. Peptide fragments of anti-HIV proteins. TCS and MMC, and other plant proteins which may be identified as having anti-HIV activity, can be cleaved by one or more of a number of sequence specific proteases, to yield peptide fragments which can be purified and tested for anti-HIV activity, according to the invention. Alternatively, segments of anti-HIV proteins with known sequence can be prepared synthetically, or by conventional recombinant techniques, and tested for anti-HIV activity.

From the foregoing, it can be appreciated how various objects and features of the invention are met. The discovery that certain plant proteins and glycoproteins effectively inhibit HIV antigen expression in both T lymphocytes and macrophages, at protein levels which are substantially non-toxic t non-infected cells, opens up a new method of treating HIV-related diseases in humans. Specifically, the treatment method attacks HIV infection at two apparently crucial fronts: First, by inhibiting expression of HIV antigen on the surface of infected blood cells, the infected cells become unable to interact and fuse with CD4+ T lymphocytes. Secondly by reducing production of viral protein by infected cells, particularly macrophages, as evidenced for example by a sharp drop in reverse transcriptase activity in infected cells, the ability of infected cells to act as reservoirs for the continued spread of the virus to healthy blood cells and other tissue, such as the CNS, is reduced.

The cell culture systems described herein provides a convenient method for selecting additional compounds which may be effective aginst HIV infection in humans. The culture systems, which may include HIV-infected T cells or monocyte/macrophagss, are sensitive to anti-HIV effects with a single exposure, and the effectiveness of test compounds can be readily assessed by the suppression of HIV antigens within a period of several days. The results with TCS and MMC suggest that effective anti-HIV compounds can produce substantially complete inhibition of viral antigens in the infected cells in a 3–6 day period. At the same time, the toxicity of the compounds to noninfected cells can be readily assessed in parallel.

The following examples illustrate various methods and uses of the present invention, and typical anti-HIV effects observed in the screening method of the invention. The examples are intented to illustrate, but in no way limit, the scope of the invention.

Materials

A. Reagents

[3]H-thymidine and $^3$H-leucine were obtained from New England Nuclear; and fluoroscein isothiocyanate (FITC) conjugated goat-anti-human lgG reagent, from Zymed (Burlingame, CA); Ribavarin, phosphonoformate, phosphonoacetate, and azidothymidine were a gift from Dr. Frank Szoka, UCSF Medical Center.

B. HIV isolate

The DV strain of HIV was used for all experiments. This is a low-passage isolate obtained from the peripheral blood of a heterosexual man with Kaposi's sarcoma (Crowe). Several liters of the high titre stock of the virus were grown in the VB T lymphoma cell line (Lifson, et al, 1986 a-c), and aliquots were stored at $-70°$ C. until used. Stock cultures of HIV-DV contained about $5\times10^5$ infectious units /ml, where an infectious unit is defined as the amount of infectious virus required to produce characteristic cytopathic effects (CPE) by day 5 of culture, when inoculated onto $5\times10^5$ VB indicator cells. Stock cultures contained about $89\times10^3$ cpm of reverse transriptase activity, as measured by published methods (Hoffman). Anti-p24 monoclonal antibody was provided by Dr. J. Carlson, UC Medical Center, Davis, CA.

C. Preparation of alpha and beta momorcharin

Decorticated dried ripe seeds (100 g) of *Momordica charantia* were homogenized in 0.9% saline (about 4 ml per 1 g) with a Waring Blender and filtered through cheesecloth. The pH of the filtrate was adjusted to 4.0 with 2 N HCl before centrifugation at 12,000 rpm for 20 min. The supernatant (crude extract) was then subjected to acetone fractionation at 4° C. To the crude extract, 0.8 v/v of cold acetone ($-20°$ C.) was slowly added with constant stirring and the mixture was kept at 4° C. for 1 h before centrifuged at 5,000 rpm for 15 min to remove the precipitate (API). Cold acetone ($-20°$ C.) was then added to the supernatant to achieve a final concentration of 2.0 v/v. After standing at 4° C. for 1 h, the mixture was centrifuged at 5,000 rpm for 15 min to recover the precipitate (APII) which was resuspended in and dialyzed against distilled water, then lyophilized. The average yield of APII from different runs was about 700 mg (0.7%).

The APII((800 mg) was dissolved in about 6 ml 0.05M phosphate buffer (pH 6.4) and applied to a column of CM-Sepharose CL-6B (Pharmacia) equilibrated with the same buffer. Initial elution was with the same buffer After the third peak had been eluted, a linear gradient of 0–0.2M NaCl in the same buffer was applied, as seen in FIG. 12A, which shows the elution profile from the column. The protein peaks designated $C_{5b}$ and $C_{6a}$ were collected, dialyzed against distilled water, and lyophilized. The average yields and percentage recoveries from APII are: $C_{5b}$ (136 mg, 17%) and $C_{6a}$ (76 mg, 9.5%).

The protein fractions $C_{5b}$ (50 mg) and $C_{6a}$ (50 mg) were separately dissolved in 2.5 ml phosphate-buffered saline (pH 7.2) and the undissolved precipitates removed by centrifugation before being applied onto a Sephadex G-100 (fine) (Pharmacia) column equilibrated and eluted with the same buffer. The major protein peaks designtted $C_5$-$G_1$ (peak $G_1$ in FIG. 12B) and $C_6$-$G_1$ (peak $G_1$ in FIG. 12C) were collected, dialyzed against distilled water and lyophilized to yield alpha-momorcharin ($C_5$-$G_1$) and beta-momorcharin ($C_6$-$G_1$), respectively. The average yields and percentage recoveries from $C_{5b}$ and $C_{6a}$ are: alpha-momorcharin (35 mg, 72%) and beta-momorcharin (32 mg, 64%).

Yields and percentage recoveries of alpha-monorcharin and beta-monorcharin from 1 kg of decorticated dried seeds of *Momordica charantia* are about 800 mg (0.08%) and 400 mg (0.04%), respectively.

D. Preparation of trichosanthin

All steps of the procedure described below were carried out at 4° C. Fresh root tubers of *T. kirilowii* were peeled, sliced into small pieces, and homogenized in a Waring blender in normal saline a pH 7 (0.7 l/kg). The homogenate was filtered through cheesecloth to eliminate debris. The extract was adjusted to pH 8 with 1N NaOH, stirred for 2 h, and then left to stand overnight. The suspension was centrifuged at 5,000 rpm for 15 min, and the resulting supernatant was lyophilized to yield the crude powder (CP).

The crude powder was then dissolved in distilled water (10 ml/g powder) and the pH of the solution was adjusted to 8 with 1N NaOH. After standing for 1 h, cold acetone (0.8 ml/ml solution) was added. A heavy precipitate resulted, and the mixture was stirred for 30 min. The precipitate (API) was collected by centrifugation at 5,000 rpm for 15 min. To the supernatant cold acetone (1.2 ml/ml supernatant) was added and after standing for 2 h, the sedimented material (AP2) was recovered by centrifugation. The two fractions AP1 and AP2 were suspended in a minimal volume of phosphate-buffered saline (PBS) and after extensive dialysis against the same buffer, the supernatant and the precipitate of each fraction were separated by centrifugation. The precipitate was then reextracted with PBS, centrifuged and the supernatant combined with the previous supernatant to form the subfraction S, while the precipitate after the reextraction formed the subfraction P. Thus, fraction AP1 gave two subfractions AP1S and AP1P. The yields of the various fractions are: about 60.5 g CP; 3.2 g AP1S; 3.8 g AP2S from 1 kg of sliced fresh tuber.

Fraction AP2S (1 g) was dissolved in about 10 ml of 0.05M poosphate buffer (pH 6.4) and applied to a column of CM-Sepharose CL-6B (Pharmacia). The column had previously been equilibrated with 0.05M phosphate buffer, and initial elution was with the same buffer. After the third peak C3 (FIG. 13A) had been eluted, a linear gradient of 0–0.3 M NaCl in the same buffer was applied, as seen in FIG. 13A. The protein peak designated C6 was collected, dialyzed against distilled water, and lyophilized to yield highly purified trichosanthin. The average yield and percentage recovery of trichosanthin from AP2S are about 180 mg (18%).

Highly purified trichosanthin was also obtained from fraction AP1S by an additional chromatographic step with DEAE-Sepharose C1-6B column. AP1S (1 g) was dissolved in 14 ml distilled water. After dialysis against 0.02 M $NH_4HCO_3$ containing 0.1 M NaCl (pH 8.0), it was ppplied to a column of DEAE-Sepharose CL-6B (1.5×32 cm) previously equilibrated with the same buffer. Column chromatography was carried out at room temperature at a flow rate of 70 ml/h and the eluate was collected in 10 ml fractions. The column was washed with 100 ml of the starting buffer (0.02M $NH_4HCO_3$) containing 0.1M NaCl and then stepwise elution was performed with 0.2M NaCl and 0.5M NaCl in the same bicarbonate buffer. Elution was monitored by absorbance at 280 nm. The eluate was pooled into four fractions D1-D4 (identified in FIG. 13B), dialyzed and lyophilized. The average yield and percentage recovery of the trichosanthin-enriched fraction D1 from AP1S is abuut 185 mg (18.5%).

The trichosanthin-enriched fraction D1 was further purified on a CM-Sepharose CL-6B column by a similar procedures as described above for AP2S. The protein peak designated P6 was collected, dialyzed against distilled water, and lyophilized to yield highly purified trichosanthin. The average yield and percentage recovery of trichosanthin from D1 (1 g) is about 445 mg (44.5%).

The combined (from AP2S and D1) yield and percentage recovery of trichosanthin from 1 kg of sliced fresh tuber of *T. kirilowii* are about 900 mg (0.09%).

EXAMPLE 1

Effect of TCS and MMC Treatment on T Cells

For assays of proliferation (thymidine incorporation) and protein synthesis (leucine incorporation) the cells were seeded at an initial concentration of $5\times10^4$ cells per well in round bottom 96 well microtiter plates in a total final volume of 200 ul of RPMI-1640 supplemented with 10% (v/v) heat inactivated fetal calf serum. Uninfected H9 cells were tested in parallel with H9 cells chronically infected with HIV (HXB-2 virus isolate). Anti-HIV agents were added to yield final concentrations ranging from 0.1 to 30 μg/ml. For assays of cellular growth and viability (trypan blue exclusion), cells were seeded at $1\times10^5$ cells per ml in 2 ml total volume per well of 12 well culture plates, with from 0.1 to 30 μg/ml (final concentration) of anti-HIV agents added. Analysis was performed 2 and/or 5 days after addition of anti-HIV agents, which were present for the duration of the culture.

A. Effects on cell growth and viability

Cell growth and viability were assessed 2 and 5 days after addition of anti-HIV agents. Cell counts were performed using a hemocytometer and viability was determined by trypan blue exclusion. As shown in FIGS. 1A and 1B, TCS and MMC treatment resulted in a concentration dependent inhibition of cellular proliferation (absolute count of viable cells/ml) at both days 2 and 5, with a preferential inhibition of the proliferation of HIV infected cells. FIG. 1C demonstrates that the percentage of viable cells in the reated cultures was decreased in a concentration dependent manner, with preferential effects on the HIV infected cells. Thus, the growth and viability of the cells appear to be impaired by both cytocidal (decreased percentage of viable cells) and cytostatic (decreased absolute cell counts and decreased percentage of viable cells) mechanisms.

B. Effects on DNA synthesis (thymidine incorporation)

To evaluate the effects of TCS and alpha-MMC on DNA synthesis, uninfected H9 cells or H9 cells chronically infected with HIV were seeded at $5\times10^4$ cells per well in round bottom microtiter plate as detailed above and cultured for 2 to 5 days in the presence of varying concentrations of the anti-HIV agents. Cells were pulsed for 12 hours before harvesting with 2 uCi per well of [$^3$H]-labeled thymidine, cells harvested on glass fiber filters, and label incorporated into cell-associated nucleic acids determined by scintillation counting. As shown in FIGS. 2A and 2B, TCS and MMC treatment resulted in a concentration dependent inhibition of cellular incorporation of [$^3$H]-thymidine, with a preferential effect against the HIV infected cells. It is not clear from these experiments whether the observed inhibition of cellular incorporation [³H]-thymidine reflects a direct inhibitory activity of the anti-HIV agents on DNA synthesis or is a secondary consequecce of decreased cell numbers resulting from the cytocidal and cytostatic effects noted above.

C. Effects on Protein Synthesis (Leucine Incorporation)

Figure 2:
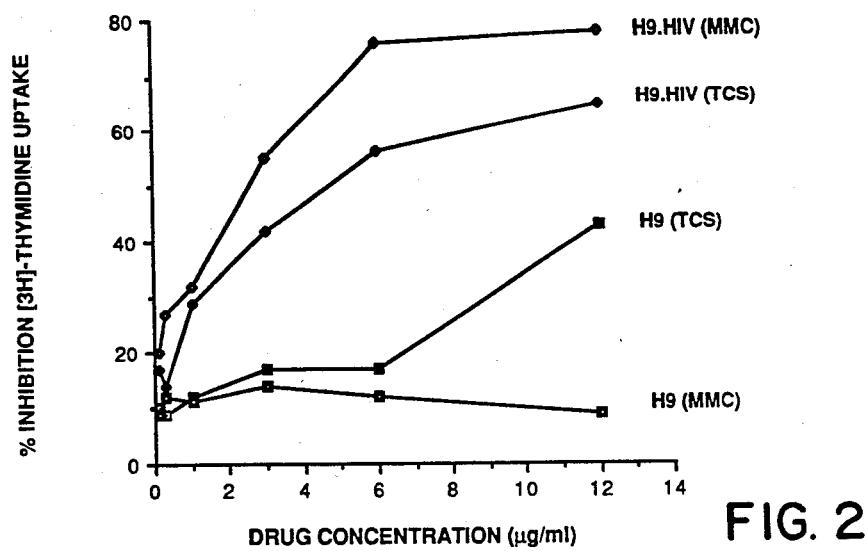
FIG. 2 shows the inhibition of [$^3$H]-thymidine incorporation by HIV-infected (diamonds) and uninfected (squares) T cells (H9 cell line) measured 2 days after initial exposure to TCS (closed symbols) and MMC (open symbols), plotted as a function of the concentration of TCS or MMC peptide added to the culture.
Figure 3:
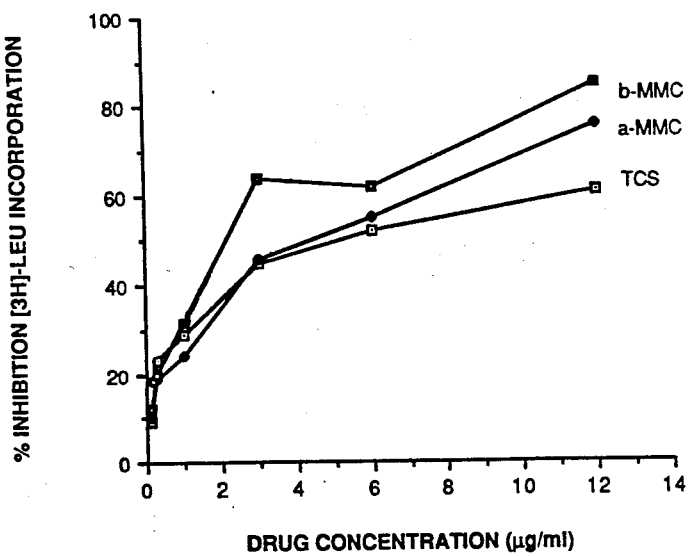
FIG. 3 shows [$^3$H]-leucine incorporation into HIV-infected T cells (H9 cell line) 2 days after addition of increasing concentrations of TCS, alpha-MMC or beta-MMC.

To determine the effects of the anti-HIV agents on protein synthesis, replicate microtiter plate cultures were set up as described above, in the presence of varying concentrations of the anti-viral substances. Cells were pulsed with 2 uCi per well of [³H]-lecine and after harvesting on glass fiber filters, inhibition of protein synthesis was measured by determining the amount of labeled leucine incorporated into trichloroacetic acid precipitable protein through scintillation counting. As shown in FIG. 2C, all of the anti-viral agents tested resulted in a concentration dependent inhibition of protein synthesis by the HIV infected cells.

EXAMPLE 2

Effects on Viral Antigen Expression: Indirect Immunofluorescence Analysis

To evaluate the effects of the anti-HIV agents on viral antigen expression (including expression of the pathogenetically significant envelope antigens gp 120 and gp 41), HIV infected H9 cells were seeded at $0.5 \times 10^6$/ml and cultured in RPMI-1640 supplemented with 10% heat inactivated fetal calf serum, in the presence of TCS or alpha-MMC at concentrations ranging from 0.3 to 10 µg/ml. Culture medium was replaced every 3-5 days with fresh medium containing additional TCS or alpha-MMC to maintain the specified concentration. At various time points, cells were assayed for expression of HIV antigens by indirect immunofluorescence analysis. Briefly, for each assay, $1 \times 10^6$ cells were washed with phosphate buffered saline containing 1% HI-FCS (staining buffer). Cells were then incubated with a 1:50 dilution of previously charaterized HIV antibody positive or negative serum in staining buffer at 4° C. for 45 minutes. After washing, bound specific antibody was detected with a fluorescein conjugated goat anti-human IgG reagent. Quantitative flow cytometric analysis was performed on an Ortho Cytofluorograf 50 H. FIGS. 4A to 4H show the results of flow cytometic analysis performed at day 16 of culture. FIGS. 4A and 4B demonstrate the lack of reactivity of the HIV antibody negative (4A) and antibody positive (4B) patient serum with uninfected H9 cells. FIGS. 4C and 4D show specific reactivity of the antibody positive serum with HIV infected cells (4D) while HIV antibody negative serum does not react (4C). The antibody negative serum does not react with HIV infected cells treated with 10 µg/ml of TCS(4E) or a-MMC (4G). The antibody positive serum shows only background levels of reactivity (approximately 2% or fewer cells showing above threshold fluorescence) with the TCS treated (4F) and a-MMC treated (4H) HIV infected cells, indicating the virtual absence of viral antigen expression by the treated cells. This dramatic phenomenon is noted most strikingly upon comparing FIG. 4D with FIGS. 4F and 4H.

EXAMPLE 3

Effect of TCS and MMC Treatment on Viral Replication in Infected T cells

Viral replication was assessed by measuring particle associated reverse transcriptase activity in cell-free supernatants of cultures. Infected and non-infected cells were seeded and exposed to several selected concentrations of TCS or alpha-MMC as above. At 2 and 5 days after exposure to the drug, the cell suspensions were collected and pelleted by centrifugation at 500×g for 10 minutes. The supernatant was then centrifuged at 45,000 g for one hour and reverse transcriptase (RT) activity was measured as described (Hoffman). Beta-momomorcharin also gave inhibition of viral replication.

The results obtained for supernatants harvested on day 5 are plotted, as a function of concentration of the drug added, in FIG. 5. Uninfected cells showed no detectable RT activity. Both TCS and MMC treatment resulted in significant, concentration dependent decreases in the amount of viral replication in the cultures, as assessed by measuring particle associated RT activity in cell free culture supernatants. At high concentrations of TCS virtually no RT activity was detected, particularly when one allows for the small amount of virus produced during the first several hours of treatment before the anti-HIV agents have had a chance to exert their effects.

EXAMPLE 4

HIV Infection of Human Macrophages

A. Culturing human macrophages

Human macrophage cultures were established from peripheral blood mononuclear cells obtained from leukophoresis preparations of human blood, and buffy coats from normal blood donars, according to established methods (Crowe). Briefly, peripheral blood mononuclear cells were isolated by density centrifugation over Ficollhypaque, and allowed to attach to glass petri dishes in RPMI 1640 medium supplemented with 20% fetal calf serum at 37° C. for 1 hour. After washing (to remove contaminating, non-adherentllymphocytes), the monocytes were recovered from the petri dishes by placing on ice for 10 minutes in 5 uM EDTA-PBS-CMF-5%FCS medium and scraping with a rubber policeman. The recovered monocyte preparation was then centrifuged, resuspended in RPMI 1640 medium with 10% pooled male HIV-negative human serum (complete medium) and placed into Teflon ® culture vessels at $2 \times 10^6$ cells per ml. Cell viability decreased over the first five days in culture to a stable density of approximately $5 \times 10^5$ cells per ml. Long term cultures were maintained at this density for up to four months. Medium was routinely changed every 7 days.

B. Percent cells infected

To infect the macrophage cells with HIV, the macrophages were pelleted by centrifugation after 5-15 days in culture, then resuspended in PBS with 2 µg/ml of polybrene, followed by incubation at 37° C. for 30 minutes. After washing and centrifugation, the pelleted cells were resuspended in HIV-DV, at a concentration of $5 \times 10^5$ macrophages and $5 \times 10^5$ infectious units pe ml. Cells were left in contact with the virus overnight at 37° C., then unbound virus was washed away, and the cells were resuspended at $5 \times 10^5$ cells per ml in complete medium.

The frequency of HIV infected macrophages was determined by cytofluorographic, single-cell, indirect immunofluorescence, as described (Crowe). Briefly, infected and uninfected macrophages were fixed with 3% formaldehyde at 40° C. for 45 minutes, then washed with PBS containing 0.2M glycine, pH 7.4, to inactivate free formaldehyde groups. Pelleted, fixed cells were resuspended on ice in 0.1% Triton X-100 to allow permeabilization of the cell membranes. Infected and uninfected macrophages were then exposed to a primary antibody—either mouse monoclonal antibody reactive specifically against HIV core protein p24, or to MOPC-21, an isotype matched control antibody of irrelevant specificity. After incubation with the primary antibody at 4° C. for 45 minutes, the cells were washed in PBS/FCS/azide medium, then incubated with FITC labeled goat anti-mouse IgG reagent, as in Example 2. Cell fluorescence was analyzed as above, where aackground staining with the MOPC-21 antibody was used to establish threshhold gating.

FIG. 6 shows plots of cell counts as a function of fluorescence level for HIV-infected cells labeled with the control antibody (A) or anti-p24 antibody. The data indicate that about 60% of the cells in the infected macrophage culture are reactivewwith anti-p24 ten days after in vitroiinfection. The level of about 40–60% infection was routinely achieved with cells from other donors.

C. Long-term cell viability

To determine whether HIV-infected macrophages continue to survive long-term in culture, the cells were examined for p24 antigen expression over a several week period. The time course of p24 expression in infected macrophage cells from 2 different donors (open circles and triangles) is plotted in FIG. 7. As seen, p24 antigen expression increases rapidly over the first two weeks following infection (time zero), then continues at a relatively high level for at least about 4 weeks. Cell viability of infected cells from the two donors (closed circles and triangle in FIG. 7) was also examined, using Trypan blue exclusion. The infected cells show almost no loss of viability of a four-week period in culture. No cytopathic effects were observed in the infected cells over the test period.

EXAMPLE 5

Effect of RT Inhibitors on HIV-Infected Macrophages

Macrophage culture cells prepared as above and obtained from one of six donors (as indicated in Table 1) were treated with anti-viral agents which have been shown previously to inhibit de novo infection of T lymphocytes by HIV virus, and to block transmission of HIV into uninfected cells. The anti-viral agents used were ribavarin, phosphonoformate, phosphonoacetate, and azidothymidine, and the concentrations used were the highest concentrations which could be be used without substantial loss of cell viability (and higher than those previously reported to inhibit T cell infection). The cultured cells were infected with HIV-DV as above at time zero, then treated with a selected concentration of the drug, indicated in Table 1, on day 2. Four to six days later, the cells were analysed for p24 antigen expression, as above, by indirect immunofluorescence. The percent infected, drug-treated cells which have above-threshhold levels of p24 antigen are indicated in the "treated-cell" column in the table. These values are compared with the percent of untreated, infected cells which show p24 antigen expression at concentrations higher than published for inhibition of T cell infection ("untreated-cell" column), to determine % reduction in antigen positive cells. The data, showing only a partial reduction in p24 expression in th cultured cells, indicate that RT inhibitors have only a moderate inhibitory effect on established infection in macrophages.

TABLE 1

| Antiviral | | donor | untreated (control) | treated | % reduction |
|---|---|---|---|---|---|
| ribavirin | 200 ug/ml | 1 | 48% | 12% | 75% |
| | | 2 | 37% | 22% | 35% |
| phosphono formate | 100 uM | 1 | 48% | 27% | 23% |
| | 300 uM | 3 | 39% | 25% | 35% |
| | 300 uM | 4 | 37% | 13% | 65% |
| | 300 uM | 5 | 14% | 3% | 78% |
| phosphono acetate | 300 uM | 1 | 48% | 27% | 43% |
| azidothymidine | 50 uM | 6 | 38% | 11% | 71% |

EXAMPLE 6

Effect of TCS and MMC on HIV-Infected Macrophaqes

Cultured macrophages prepared as above were carried in culture for days, then exposed to TCS or MMC, at a final concentration of 5 μg/ml. Four days after addition of the drug, the cells were examined for p24 expression, as above, by indirect immunofluorescence with anti-p24 antibody. FIG. 8 shows the cytofluorographic profile of (A) control (uninfected) cells, (B), infected cells which were not exposed to drug, (C) infected, TCS-treated cells, and (D) infected, MMC-infected cells. As seen, four days after treatment with either drug reduces p24 expression in infected cells to near background levels.

EXAMPLE 7

Time Course of TCS and MMC Action on HIV-Infected Macrophages

Cultured macrophages infected with HIV were treated with 5μg/ml of TCS or MMC as in Example 6. At 1 and 4 days after addition of the drug, the cells were examined for expression of p24 antigen, by the above indirect immunofluorescence method. The data plotted in FIG. 9 show that about ⅔ of inhibition of p24 antigen expression occurs within 24 hours for both TCS (open triangles) and MMC (open circles). RT activity, measured as above, was also markedly decreased after 24 hours in cells treated with either drug. By day four, both p24 expression and RT activity were reduced to background levels, whereas untreated, but infected cells showed no decrease in p24 expression (closed circles in FIG. 9) and no decrease in RT activity. Cell viability, as measured by the Trypan blue exclusion test, was reduced to between about 60–70% during the four-day treatment with either drug.

EXAMPLE 8

Dose Response to TCS and MMC

TCS or MMC was added to cultures of the infected cells at dose levels of either 0.5 or 5 μg/ml. The cells were examined for p24 expression four days after addition of the selected drug, as in Examples 4–8 above. The results are plotted in FIG. 10. As seen, both drug concentrations gave nearly complete inhibition of p24 expression four days after addition of either TCS (crosses) or MMC (open circles). Cell viability was reduced llightly at a higher concentration of TCS, and more significantly, tt higher concentrations of MMC (data not shown).

Although specific embodiments, uses and methods of the invention have been described, it will be recognized that various changes, and modifications may be made without departing from the invention.

It is claimed:

1. A method of inhibiting expression of HIV antigens in human T lymphocytes and monocyte/macrophage cells infected with HIV, comprising exposing the infected cells to an anti-HIV protein selected from the group consisting of trichosanthin or momorcharin, at a protein concentration which is effective to produce a substantial reduction in viral antigen expression in HIV-infected cells.

2. The method of claim 1, whrein the concentration of the anti-HIV protein is between about 0.05 to 10 µg/ml, and is effective in vitro in selectively reducing the number of viable HIV-infected cells, relative to noninfected cells of the same type.

3. The method of claim 1, for use in inhibiting HIV replication in the infected cells, as evidenced by a reduction, several days after exposure to the anti-HIV protein, in reverse transcriptase associated with the infected cells.

4. The method of claim 1, wherein one of the HIV antigens which is inhibited is HIV envelope protein gp120, as evidenced by reduced binding to infected T cells of an anti-HIV antibody present in the serum of an HIV-seropositive individual.

5. The method of claim 1, wherein one of the HIV antigens which is inhibited is HIV core protein p24, as evidenced by reduced binding of anti-p24 antibodies to permeabilized HIV-infected monocyte/macrophages.

6. A method of treating a human subject infected with HIV, comprising administering to the subject a dose of an anti-HIV protein selected from the group consisting of trichosanthin and momorcharin, at a concentration of anti-HIV protein sufficient to produce a substantial reduction in viral antigen expression in the patient's HIV-infected cells.

7. The method of claim 6, wherein the anti-HIV protein is administered in parenteral form.

8. The method ff claim 7, wherein the amount of anti-HIV protein administered, as a single dose, is between about 1.5 to 15 mg.

9. The method of claim 7, wherein the drug is administered repeatedly, at suitable intervals, until a desired reduction in viral antigen expression is achieved.

10. The method of claim 7, wherein the reduction in viral antigen is evidenced by reduced binding to the subject's infected T cells of an anti-HIV antibody present in the serum of an HIV-seropositive individual.

11. The method of claim 7, wherein the reduction in viral antigen is evidenced by reduced binding of anti-p24 antibodies to permeabilized HIV-infected monocyte/macrophages derived from the subject.

12. The method of claim 6, which further includes repeating said administering at suitable intervals, assaying the subject for the presence of antibody against the administered protein, and administering a second anti-HIV protein selected from the same group if antibody against the first-administered protein is detected.

13. The method of claim 6, wherein the concentration of anti-HIV protein is sufficient to effect a selective reduction in the number of HIV-infected cells, relative to uninfected cells of the same type.

* * * * *